US011741557B2

(12) United States Patent
Mimassi

(10) Patent No.: US 11,741,557 B2
(45) Date of Patent: Aug. 29, 2023

(54) BIOMARKER-BASED FOOD ITEM DESIGN SYSTEM AND METHOD

(71) Applicant: RockSpoon, Inc., San Jose, CA (US)

(72) Inventor: Nagib Georges Mimassi, Palo Alto, CA (US)

(73) Assignee: ROCKSPOON, INC., San Jose, CA (US)

( * ) Notice: Subject to any disclaimer, the term of this patent is extended or adjusted under 35 U.S.C. 154(b) by 0 days.

(21) Appl. No.: 17/695,697

(22) Filed: Mar. 15, 2022

(65) Prior Publication Data

US 2022/0207628 A1 Jun. 30, 2022

Related U.S. Application Data

(63) Continuation-in-part of application No. 17/005,012, filed on Aug. 27, 2020, now Pat. No. 11,276,129, which is a continuation-in-part of application No. 16/993,488, filed on Aug. 14, 2020, now abandoned.

(60) Provisional application No. 62/984,237, filed on Mar. 2, 2020, provisional application No. 62/956,289, filed on Jan. 1, 2020.

(51) Int. Cl.
*G06Q 50/12* (2012.01)
*G01N 33/66* (2006.01)
*G06Q 30/0601* (2023.01)

(52) U.S. Cl.
CPC .............. *G06Q 50/12* (2013.01); *G01N 33/66* (2013.01); *G06Q 30/0631* (2013.01)

(58) Field of Classification Search
CPC ........... G06Q 30/0631; G06Q 10/0832; G06Q 10/08355; G06Q 30/0621; G06Q 30/0635; G06Q 10/06312
See application file for complete search history.

(56) References Cited

U.S. PATENT DOCUMENTS

| | | | | |
|---|---|---|---|---|
| 6,204,763 B1 * | 3/2001 | Sone | ..................... | G06Q 10/087 340/5.1 |
| 6,735,479 B2 * | 5/2004 | Fabian | ................. | A61B 5/0031 128/903 |
| 6,811,516 B1 * | 11/2004 | Dugan | ............... | G06Q 30/0623 705/26.5 |
| 7,024,369 B1 * | 4/2006 | Brown | ................... | G16H 20/70 600/513 |

(Continued)

OTHER PUBLICATIONS https://developers.google.com/machine-learning/guides/text-classification/step-3 (Year: 2022).*

(Continued)

*Primary Examiner* — Ashford S Hayles
(74) *Attorney, Agent, or Firm* — Galvin Patent Law LLC; Brian R. Galvin; Brian S. Boon

(57) ABSTRACT

A system and method for biomarker-based personalized food item design. The system is a cloud-based network containing an API connector, portals for restaurants and patrons, to enter their information, and machine learning engine which creates a unique dietary experience for patrons based on a multitude of variables associated with the business enterprises, user biomarker data, a user specific biomarker goal, dietary needs, ingredient information, and preferences both explicit and inferred. The system may be accessed through web browsers or purpose-built computer and mobile phone applications.

12 Claims, 16 Drawing Sheets

(56) References Cited

U.S. PATENT DOCUMENTS

| | | | | |
|---|---|---|---|---|
| 7,065,501 | B1* | 6/2006 | Brown | G06Q 20/203 705/28 |
| 7,979,309 | B1* | 7/2011 | Stevens | G06Q 30/0641 705/26.7 |
| 8,036,912 | B2* | 10/2011 | Jensen | G16H 20/60 705/2 |
| 8,249,946 | B2* | 8/2012 | Froseth | G06Q 10/101 426/103 |
| 8,321,302 | B2* | 11/2012 | Bauer | H01Q 7/00 705/28 |
| 9,159,088 | B2* | 10/2015 | Dillahunt | G06Q 30/0261 |
| 9,412,086 | B2* | 8/2016 | Morse | G06K 7/1417 |
| 10,474,661 | B2* | 11/2019 | Knobel | G06Q 10/087 |
| 2002/0026363 | A1* | 2/2002 | Dunaway, Jr. | G06Q 30/02 705/15 |
| 2002/0027164 | A1* | 3/2002 | Mault | G16H 20/30 235/462.46 |
| 2003/0158796 | A1* | 8/2003 | Balent | G06Q 30/06 705/28 |
| 2005/0113649 | A1* | 5/2005 | Bergantino | G16H 20/10 600/300 |
| 2006/0074716 | A1* | 4/2006 | Tilles | G16H 20/60 705/2 |
| 2006/0178947 | A1* | 8/2006 | Zsigmond | G06Q 30/0601 705/37 |
| 2009/0075242 | A1* | 3/2009 | Schwarzberg | G09B 19/0092 434/127 |
| 2009/0099873 | A1* | 4/2009 | Kurple | G16H 20/60 705/3 |
| 2009/0234839 | A1* | 9/2009 | Angell | G06Q 10/04 707/999.005 |
| 2009/0275002 | A1* | 11/2009 | Hoggle | G16H 20/60 707/999.1 |
| 2009/0276487 | A1* | 11/2009 | Jensen | G16H 20/60 709/203 |
| 2010/0136508 | A1* | 6/2010 | Zekhtser | G16H 20/60 434/127 |
| 2010/0138203 | A1* | 6/2010 | Alferness | G16H 20/17 703/11 |
| 2011/0055044 | A1* | 3/2011 | Wiedl | G06Q 30/0282 705/347 |
| 2011/0167100 | A1* | 7/2011 | Brodowski | G06F 17/00 708/133 |
| 2012/0016781 | A1* | 1/2012 | Hashimoto | G06Q 10/087 705/29 |
| 2012/0059664 | A1* | 3/2012 | Georgiev | A61B 5/021 705/2 |
| 2012/0072233 | A1* | 3/2012 | Hanlon | G16H 20/60 705/2 |
| 2012/0094258 | A1* | 4/2012 | Langheier | G16H 20/30 434/127 |
| 2012/0101876 | A1* | 4/2012 | Turvey | G06Q 40/00 705/14.1 |
| 2012/0130732 | A1* | 5/2012 | Blander | G16H 20/30 705/2 |
| 2012/0183932 | A1* | 7/2012 | Chang | G09B 5/125 434/127 |
| 2013/0138656 | A1* | 5/2013 | Wheaton | G06Q 30/06 709/219 |
| 2013/0218511 | A1* | 8/2013 | Mager | G06Q 10/087 702/129 |
| 2013/0280681 | A1* | 10/2013 | Narayan | G16H 20/60 434/127 |
| 2014/0095479 | A1* | 4/2014 | Chang | G06Q 30/0631 707/E17.005 |
| 2014/0127651 | A1* | 5/2014 | Brazell | G16H 20/60 434/127 |
| 2014/0255882 | A1* | 9/2014 | Hadad | G09B 19/0092 434/127 |
| 2015/0120317 | A1* | 4/2015 | Mayou | G16H 40/63 705/2 |
| 2016/0232625 | A1* | 8/2016 | Akutagawa | H04L 51/214 |
| 2016/0239624 | A1* | 8/2016 | Short | A61B 3/113 |
| 2017/0061392 | A1* | 3/2017 | Meza-Guinea | G06Q 50/12 |
| 2017/0109806 | A1* | 4/2017 | Adoni | G06Q 30/0631 |
| 2017/0286625 | A1* | 10/2017 | Blander | G16H 50/30 |
| 2017/0372197 | A1* | 12/2017 | Baughman | G06N 3/047 |
| 2018/0144820 | A1* | 5/2018 | Grimmer | G16H 20/60 |
| 2018/0189636 | A1* | 7/2018 | Chapela | G06F 1/163 |
| 2018/0240359 | A1* | 8/2018 | Hujsak | G06N 5/022 |
| 2018/0293638 | A1* | 10/2018 | Simpson | G06Q 30/0633 |
| 2018/0374567 | A1* | 12/2018 | Toumazou | G16H 20/60 |
| 2019/0221303 | A1* | 7/2019 | Bennett | G16H 10/20 |
| 2019/0244541 | A1* | 8/2019 | Hadad | G16H 20/60 |
| 2019/0290172 | A1* | 9/2019 | Hadad | G06N 20/00 |
| 2019/0304000 | A1* | 10/2019 | Simpson | G16B 40/00 |
| 2020/0005928 | A1* | 1/2020 | Daniel | G16H 15/00 |
| 2020/0042865 | A1* | 2/2020 | Lee | G06N 3/084 |
| 2020/0066181 | A1* | 2/2020 | Hadjigeorgiou | G16H 20/60 |
| 2020/0098466 | A1* | 3/2020 | Murdoch | G16H 20/60 |
| 2020/0131581 | A1* | 4/2020 | Jain | G16H 50/20 |
| 2020/0234810 | A1* | 7/2020 | Athey | G16B 45/00 |
| 2020/0245913 | A1* | 8/2020 | Dalal | G16H 50/20 |
| 2020/0364588 | A1* | 11/2020 | Knox | G06V 40/20 |
| 2021/0035658 | A1* | 2/2021 | Neumann | G16C 20/70 |
| 2021/0118545 | A1* | 4/2021 | Sathyanarayana | G06N 20/20 |
| 2021/0233663 | A1* | 7/2021 | Nazem | G16H 50/20 |

OTHER PUBLICATIONS

Kourajian, J. B. (2015). Relationships among diet quality, BMI and cooking skills in a group of college students (Order No. 1592606). Available from ProQuest Dissertations & Theses Global. (1708672942). (Year: 2015).*

Anderson, Carl. "A survey of food recommenders." arXiv preprint arXiv:1809.02862 (2018). (Year: 2018).*

* cited by examiner

501 Convert patron related food item text documents to corresponding word vectors.

502 Convert restaurant related recipe and culinary preparation skill text documents to corresponding word vectors.

503 Compare the resultant Patron word vector with the Restaurant word vector using term vector space techniques.

504 Select the Restaurant word vector that is most similar to the Patron food-item requirement.

505 Modify restaurant recipe items based on restaurant ingredients, culinary capabilities to most closely align to patron's requirements.

506 Output Food Item Recipe to Patron and Restaurant devices.

Fig. 5

BIOMARKER-BASED FOOD ITEM DESIGN SYSTEM AND METHOD

CROSS-REFERENCE TO RELATED APPLICATIONS

Priority is claimed in the application data sheet to the following patents or patent applications, the entire written description of each of which is expressly incorporated herein by reference in its entirety:
Ser. No. 17/005,012
62/984,237
Ser. No. 16/993,488
62/956,289

BACKGROUND

Field of the Art

The disclosure relates to the field of computerized comparative and artificial intelligent systems, and more particularly to the field of computerized systems for food item personalization, optimization, business selection, food ordering, for retail business establishments and its patrons.

Discussion of the State of the Art

People frequently wishing to dine at a retail business establishment are limited to ordering and consuming a limited set of food items based on a restaurants long standing menu with limited manual customization that take into account a patron's dietary preferences or desired long-term outcomes. Similarly, restaurants are not free to dynamically change menu items based on ingredients on hand and/or culinary skills available that maximizes their business outcomes and impact on a particular patron and/or prospective patron dining experience. The result is often a suboptimal dining experience for restaurant consumers and reduced long term viability for the restaurant.

Additionally, the proliferation of devices which can provide continuous, real-time information streams regarding biomarkers associated with device users has substantially increased the quantity of available biomarker data. The food that an individual consumes has a direct impact on their health and lifestyle outcomes, the results of which can be measured via biomarker data.

There is currently no automated system that personalizes and optimizes food item recommendations based on user biomarker data.

What is needed is a system and method for biomarker-based personalized food item design.

SUMMARY

Accordingly, the inventor has conceived, and reduced to practice, a system and method for biomarker-based personalized food item design. The system is a cloud-based network containing an API connector, portals for restaurants and patrons, to enter their information, and machine learning engine which creates a unique dietary experience for patrons based on a multitude of variables associated with the business enterprises, user biomarker data, a user specific biomarker goal, dietary needs, ingredient information, and preferences both explicit and inferred. The system may be accessed through web browsers or purpose-built computer and mobile phone applications.

According to a preferred aspect, a system for biomarker-based personalized food item design, comprising: a computing device comprising a memory, a processor, and a non-volatile data storage device; a recipe database stored on the non-volatile data storage device, the recipe database comprising a plurality of recipes, each recipe comprising a food type, a list of required ingredients and for each ingredient nutritional information; a user profile database stored on the non-volatile data storage device, the user profile database comprising a plurality of user profiles, each user profile comprising user preferences; a machine learning algorithm configured to identify associations among the user preferences, biomarker data, and the nutritional information; a machine learning engine comprising a first plurality of programming instructions stored in the memory of, and operating on the processor of, the computing device, wherein the first plurality of programming instructions, when operating on the processor, causes the computing device to: receive, from a measurement device, biomarker data associated with a user of the measurement device; convert the user preferences, recipes, food items, nutritional information, and biomarker data into a first set of vector representations; pass the vector representations through the machine learning algorithm to identify associations among the user preferences, biomarker data, and the nutritional information; receive, from a user mobile device, a user specified biomarker goal; convert the user specified biomarker goal into a second set of vector representations; pass the second set of vector representations through the machine learning algorithm to obtain a best fit between the user specified biomarker goal and the identified associations, the best fit comprising a recommended food item; and send the food item recommendation to the user mobile device.

According to another preferred aspect, a method for biomarker-based personalized food item design, comprising the steps of: storing a recipe database on a non-volatile data storage device of a computing device comprising a memory, a processor, and the non-volatile storage device, the recipe database comprising a plurality of recipes, each recipe comprising a food type, a list of required ingredients and for each ingredient nutritional information; storing a user profile database on the non-volatile storage device, the user profile database comprising a plurality of user profiles, each user profile comprising user preferences; configuring a machine learning algorithm to identify associations among the user preferences, biomarker data, and the nutritional information; using a machine learning engine operating on the computing device to: receive, from a measurement device, biomarker data associated with a user of the measurement device; convert the user preferences, recipes, food items, nutritional information, and biomarker data into a first set of vector representations; pass the vector representations through the machine learning algorithm to identify associations among the user preferences, biomarker data, and the nutritional information; receive, from a user mobile device, a user specified biomarker goal; convert the user specified biomarker goal into a second set of vector representations; pass the second set of vector representations through the machine learning algorithm to obtain a best fit between the user specified biomarker goal and the identified associations, the best fit comprising a recommended food item; and send the food item recommendation to the user mobile device.

According to an aspect of an embodiment, the biomarker data comprises biological, physiological, and/or behavioral information.

According to an aspect of an embodiment, the measurement devices comprise sensors embedded in the user mobile device and wearable technologies.

According to an aspect of an embodiment the user preference is based on nutritional data retrieved from a third-party resource over a network.

According to an aspect of an embodiment, the user specified biomarker goal is to regulate biomarker outcomes.

According to an aspect of an embodiment, the biomarker outcomes are regulated to lower, maintain, or raise biomarker measurements.

BRIEF DESCRIPTION OF THE DRAWING FIGURES

The accompanying drawings illustrate several aspects and, together with the description, serve to explain the principles of the invention according to the aspects. It will be appreciated by one skilled in the art that the particular arrangements illustrated in the drawings are merely exemplary, and are not to be considered as limiting of the scope of the invention or the claims herein in any way.

FIG. 5 is a flow diagram showing the steps of an exemplary method for an optimized food item recipe generation process based on a particular patron current food preferences, historical culinary transactions, current geographic location, and the restaurant's ingredients on hand and culinary skills.

DETAILED DESCRIPTION

Figure 1:
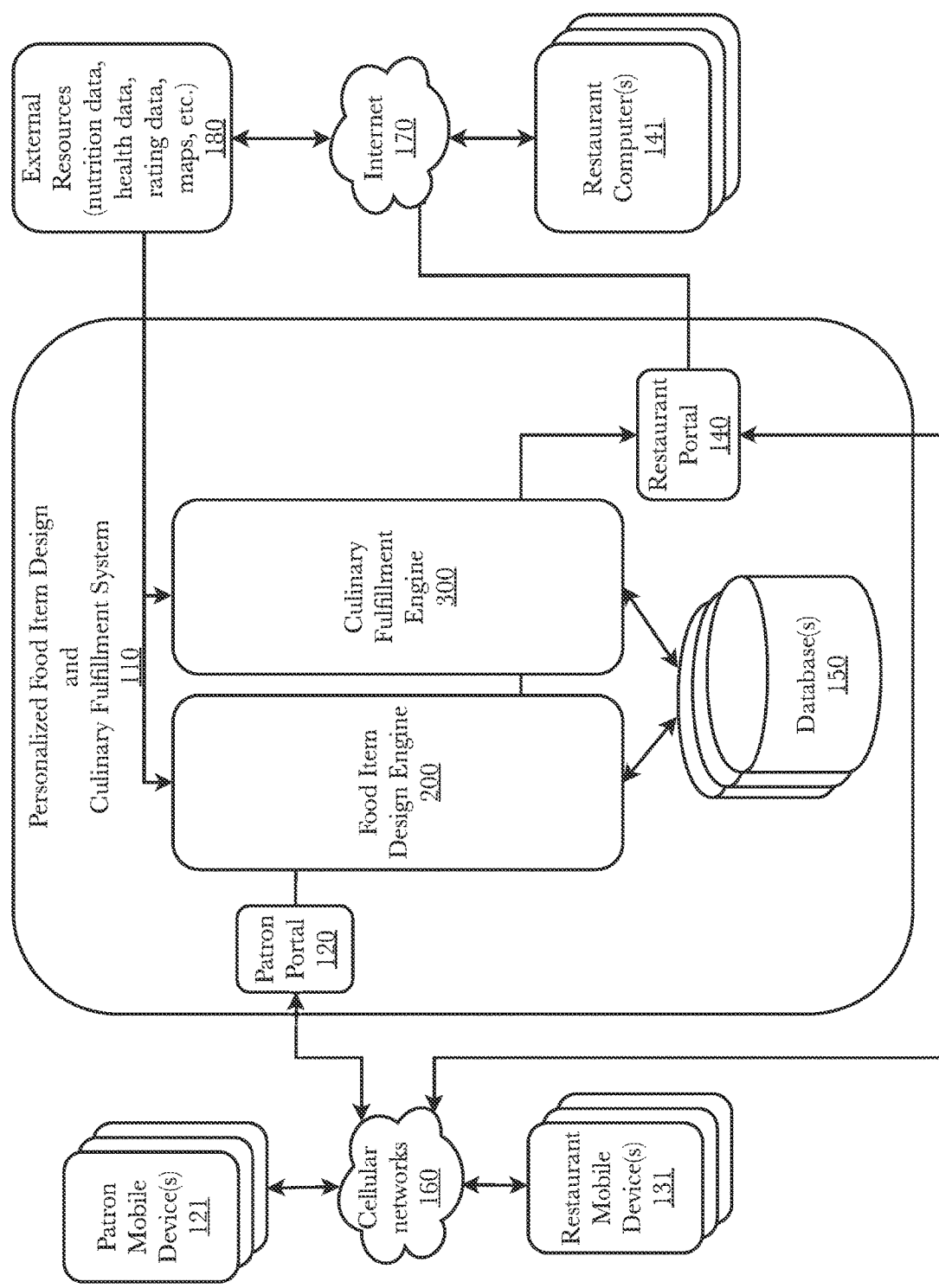
FIG. 1 is a block diagram illustrating an exemplary system architecture for an automated personalized food item design and culinary fulfillment system.

The inventor has conceived, and reduced to practice, a system and method for biomarker-based personalized food item design. The system is a cloud-based network containing an API connector, portals for restaurants and patrons, to enter their information, and machine learning engine which creates a unique dietary experience for patrons based on a multitude of variables associated with the business enterprises, user biomarker data, a user specific biomarker goal, dietary needs, ingredient information, and preferences both explicit and inferred. The system may be accessed through web browsers or purpose-built computer and mobile phone applications.

It is frequently the case that a person wishes to order food from a restaurant that meets a set of explicit requirements (e.g. healthy, fast, good price value, etc.) as well as an implicit requirement (reputable establishment, high quality ingredients, etc.). Additionally, the person has longer term nutritional goals (e.g. maintain healthy weight, blood pressure, energy level, etc.) that should be taken in consideration as they decide where and what to dine on. However, achieving the desired outcome using currently available tools is difficult and in doing so often results in a suboptimal experience for the patron and loss of viability for the business. The person could select a restaurant by chance, usually by seeing a sign for a restaurant while driving. Alternately, they could try to find a restaurant by searching using a mobile device. In this case, the person first has to open an application, search for nearby restaurants, and select a restaurant by clicking on it. However, in doing so, the decision is, again, based largely on chance, as the driver is forced to make a restaurant selection from restaurants shown in the nearby area and based only on the restaurant name, which may or may not indicate a type of cuisine (e.g., Italian food, American food, Mexican food, Japanese food, etc.). If the person wishes to get additional information, such as menu options, pricing, etc., the person is forced to take additional steps and time to researching restaurant websites, opening up menus, or calling the restaurant for more information. All of these methods are inefficient and none of them takes into account a myriad of factors that may affect the decision such as the person's current food preferences, historical culinary transactions, restaurants ingredients on hand and culinary skills available.

The invention is particularly useful to both restaurants and their patrons in personalizing and optimizing the dining experience. Personalized food item design enables restaurants to differentiate themselves by offering a unique menu that caters to their patron's needs while optimizing the food ingredients and culinary skills on hand. Patrons can select food items based on their current and past dietary requirements and preferences. As will be further disclosed herein, the invention makes a multivariate analysis of a large variety of factors (patron preferences; restaurant location, ingredient on-hand, culinary skill; social validation; etc.) to allow a patron to gain access to personalized food items fulfilled by convenient restaurant selection which optimize their dining experience and longer term dietary goals.

While the use case of patrons searching for food at a dining establishment is a primary example used herein, it is important to note that the invention is not so limited, and may be used by any person (e.g., person preparing food from home) seeking to purchase food items or ingredients at any retail business establishment (i.e., the invention is not limited to restaurants, and can be applied to any retail goods, such as grocery stores, on-line and/or brick and mortar; home food inventory).

One or more different aspects may be described in the present application. Further, for one or more of the aspects described herein, numerous alternative arrangements may be described; it should be appreciated that these are presented for illustrative purposes only and are not limiting of the aspects contained herein or the claims presented herein in any way. One or more of the arrangements may be widely applicable to numerous aspects, as may be readily apparent from the disclosure. In general, arrangements are described in sufficient detail to enable those skilled in the art to practice one or more of the aspects, and it should be appreciated that other arrangements may be utilized and that structural, logical, software, electrical and other changes may be made without departing from the scope of the particular aspects. Particular features of one or more of the aspects described herein may be described with reference to one or more particular aspects or figures that form a part of the present disclosure, and in which are shown, by way of illustration, specific arrangements of one or more of the aspects. It should be appreciated, however, that such features are not limited to usage in the one or more particular aspects or figures with reference to which they are described. The present disclosure is neither a literal description of all arrangements of one or more of the aspects nor a listing of features of one or more of the aspects that must be present in all arrangements.

Headings of sections provided in this patent application and the title of this patent application are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible aspects and in order to more fully illustrate one or more aspects. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other aspects need not include the device itself.

Techniques and mechanisms described or referenced herein will sometimes be described in singular form for clarity. However, it should be appreciated that particular aspects may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various aspects in which, for example, functions may be executed out of order from that shown or discussed, including substantially concurrently or in reverse order, depending on the functionality involved, as would be understood by those having ordinary skill in the art.

Definitions

"Business establishment" or "place of business" as used herein mean the location of any business entity with which customers may transact business. Typically, this will be a physical location where customers may enter the location and transact business directly with employees of the business, but may also be a delivery-based business. Many examples herein use a restaurant as the business establishment, but the invention is not limited to use in restaurants, and is applicable to any business establishment. "Patron" is used to reference the customer or prospective customer of the business establishment.

"Biomarker" as used herein means a defined characteristic that is measured as an indicator of normal biological processes, condition, pathogenic processes, or responses to an exposure or intervention, including therapeutic interventions. Within the context of this disclosure exposures or interventions may indicate a recommended food item that may be consumed by a system user in order to raise, maintain, or lower one or more of a plurality of biomarkers and/or biomarker outcomes associated with the system user. As a simple example, a blood glucose biomarker for a diabetic user may be regulated by consuming recommended food items, wherein the recommended food items are based on nutritional information associated with the ingredients of the food item, biomarker data associated with the diabetic user, and a user specified goal (e.g., maintain blood glucose level above a certain threshold, etc.).

Conceptual Architecture

FIG. 1 is a block diagram illustrating an exemplary system architecture 100 for a personalized food item design and culinary fulfilment system, according to a preferred aspect. According to an aspect, and using a restaurant as an exemplary business establishment, system 100 comprises a food item design engine 200, a patron portal 120, a restaurant portal 140, databases 150, and a culinary fulfillment engine 300. Patron mobile devices 121 may connect to patron portal 120, typically via a cellular phone network 160, although connections may be made through other means, as well, such as through Internet 170 (e.g., through a Wi-Fi router). Restaurant computers 141 and/or restaurant mobile devices 131 may connect to restaurant portal 140, typically through an Internet 170 connection, although other network connections may be used.

According to an aspect, a patron may be enroute to a destination, such as her home. The patron may connect to patron portal 120 to pre-enter a variety of preferences and other information that may be stored in a database 150, and used by food item design engine 200 to suggest personalized food items that meet the patron's preferences. Examples of the types of preferences that a patron may enter include, but are not limited to: food preferences such as types of food (e.g. ethnicity such as Chinese, American, Greek, as well as for example style such as spicy or soup and salad or steakhouse fare, etc.), frequency with which preferred foods are eaten, ranking of particular foods relative to other foods, patrons inconvenience preferences such as time delays and distance/time required of detour, food attributes such as price, calories, ingredients, and side dishes. In some aspects, certain of these preferences may be determined by system 100. For example, the types of food preferred by the patron and the frequency with which preferred foods are eaten may be determined based on the culinary transaction history of usage or stored in a database 150 in the system. Other such preferences and factors may also be determined by system through access to one or more external resources 180 such as a health service provider that may include known food allergies, blood pressure history, diabetic information and so forth. Other exemplary external resources may comprise research organizations such as National Library of Medicine, government data sources such as data.gov, corporate sources such as Registry of Open Data (RODA) on Amazon Web Services Likewise, restaurants may connect to restaurant portal 140 to enter information about the restaurant and its menu. Examples of the types of information that a restaurant may enter include, but are not limited to: restaurant name, location, types of food offered, hours of operation, phone number, specific menu offerings, food preparation times for certain dishes (including adjustments to food preparation times during busy periods for the restaurant), prices, calorie counts, ingredients, side dishes, drinks, and special pricing options like daily "happy hour" specials or seasonal offerings. In some aspects, the system may be able to determine certain restaurant information by accessing external resources 180 such as mapping websites and applications. For example, system may access a publicly-available mapping website such as Google maps, which may contain information about the restaurant's name, location, types of food offered, hours of operation, phone number, etc. Thus, in some aspects, it is not necessary for the restaurant to enter certain information through portal, as the information may be automatically obtained from external resources 180.

When a patron mobile device 121 connects to personalized food item design and culinary fulfilment system 110 and the patron requests en-route food item assistance, food item design engine 200 retrieves the patron preferences from a database 150. The patron may further enter additional food item preferences and a destination or select a pre-entered destination presented from the patron's preferences through patron real-time update engine 211, which will allow the system to better customize its restaurant suggestions. A culinary fulfilment engine 300 then determines the patron's location by querying the patron's mobile device for location information (e.g., provided by the mobile device's GPS hardware, Wi-Fi location applications, etc.) and gathers information from external resources 180 about restaurant options located nearby and along the route from the patron's currently location to the patron's destination, as well as traffic information related to the patron's location, intended route, and identified restaurant options. A culinary fulfilment engine 300 retrieves additional information from a database about identified restaurant options, if such information is available. Based on the patron preferences, restaurant information, and traffic information, culinary fulfilment engine 300 identifies one or more restaurants and one or more food options available at those restaurants that are compatible with the patron's preferences, and presents the identified restaurants and their corresponding food options to the patron on the patron's mobile device 121 as suggestions along with indications of the additional delay that will be caused by choosing each suggestion.

In some aspects, an application on patron's mobile device 121 may dial the phone number of the chosen restaurant for the patron to place the order via voice and combination of text message. In an aspect, culinary fulfilment server 300 will contact the restaurant through restaurant portal 140 to automatically enter an order into the restaurant's computer 141, or to direct an employee of the restaurant to call the patron's mobile device 121, or to establish a voice connection between the restaurant and the patron's mobile device 121 through another means (e.g., voice over internet protocol, or VOIP).

In some aspects, culinary fulfilment engine 300, through restaurant portal 140, may also provide information to the restaurant to schedule the restaurant's food preparation activities to coordinate with the patron's arrival. If the restaurant has entered information such as food preparation times, culinary fulfilment engine 300 may use that information to instruct the restaurant's kitchen staff when to start preparation of the patron's order, such that the order will be ready just prior to arrival of the patron. Such food preparation times and scheduling may be adjusted for busy periods at the restaurant (typically around lunch and dinner) either automatically based on the restaurant's history as stored in a database 150, or by retrieving information stored in a database 150 that has been manually entered by the restaurant through restaurant portal 140.

Figure 2:
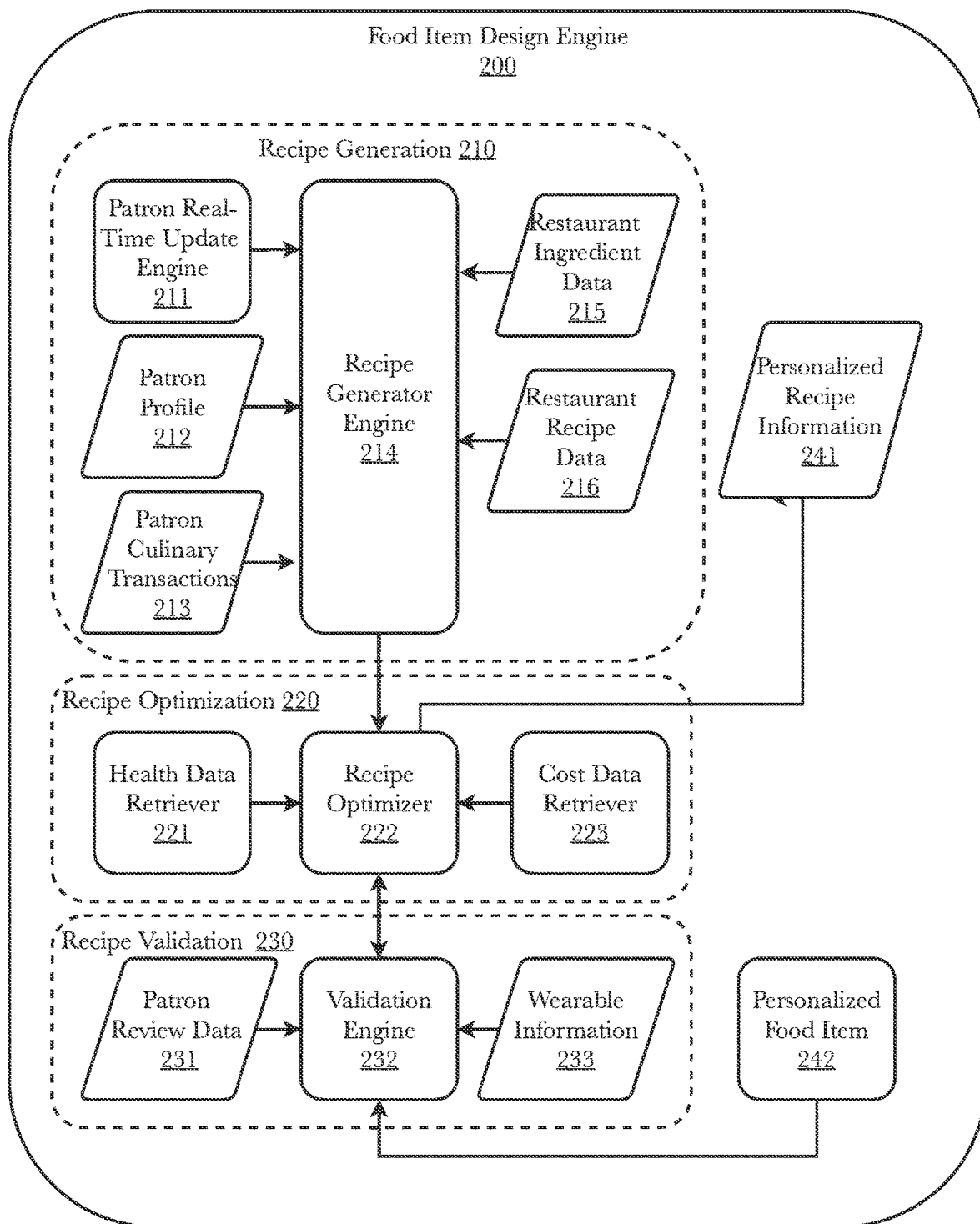
FIG. 2 is a block diagram illustrating an exemplary architecture for an aspect of an automated food item design engine.

FIG. 2 is a block diagram illustrating an exemplary architecture for an aspect of an automated food item design engine 200. According to an aspect, a food item design engine 200 comprises several subsystems, a recipe generation subsystem 210, a recipe optimization subsystem 220, and aa recipe validation subsystem 230. A recipe generation subsystem comprises a patron real-time update engine 211, a patron profile 212, patron culinary transaction 213, recipe generator engine 214, restaurant ingredient data 215, and restaurant recipe data 216. A patron real-time update engine 211 enables the patron to provide up-to-date food item input by the patron using an application on his or her mobile device 131. A patron profile 212, patron culinary transactions 213, restaurant ingredient data 215, and restaurant recipe data 216 may be retrieved from a database 150 or, in some aspects, obtained from external resources 180.

A recipe optimization subsystem comprises a recipe optimizer 222, a health data retriever 221, and a cost data retriever 223. A health data retriever 221 obtains health data from external sources 180, that may include a health provider system, while a cost data retriever 223 may either obtain cost data from a database 150 or from external resources 180.

A recipe validation subsystem 230 comprises patron review data 231, a validation engine 232, and wearable data 233. A validation engine may take as input patron review data, wearable data and personal food item information; and provides as output updates to a food item recipe to a recipe optimizer 222.

In operation, when a patron is desiring food item assistance a recipe generator engine 214 receives the patron's current food item requirements from a patron real time update engine 211 along with a patron profile 213. A recipe generation engine 214 obtains restaurant ingredient data 215 and restaurant recipe data 216 for one or more restaurants either from a database 150 or from external resources 180. A recipe generation engine 214 then uses machine learning algorithms to create a personalized food item optimized to meet the patron preferences and outcomes.

A recipe generator engine 214 presents recommendations to the patron about food items meeting the patron's preferences and allows the patron to select an option on his or her mobile device 121 by simply selecting an option (on a touch-based mobile device interface, for example). A recipe generator engine 214 then sends the information about the selected recipe to a recipe optimizer 222, which obtains health data from health data retriever 221 and cost from cost data retriever 223 and optimizes the recipe. Optimization may occur around one or more parameters including health, cost, restaurant dining experience, etc. depending on patrons near and long-range goals and stated outcomes. Once complete, recipe optimizer engine 222 sends personalized recipe information 241 to a culinary fulfillment engine 300.

In some aspects, food item design 200 engine may have a recipe validation subsystem 230, in which a validation engine 232 receives feedback from the patron's experience from patron review data 231 and patrons wearable information 233 and associates with a personalized food item 242. The feedback in the form of subjective text comments and/or objective measurements (e.g. blood pressure, glucose levels) may then be updated in the patron's culinary transactions 213 for use in future food item optimization.

Note that this example is simplified for clarity, and that food item design engine 200 will address a much broader set of factors and variables, as described elsewhere herein. The food item design engine may use any number of optimization algorithms, including machine learning algorithms or others known in the art, to find optimal solutions to the large number of variables presented.

Figure 3:
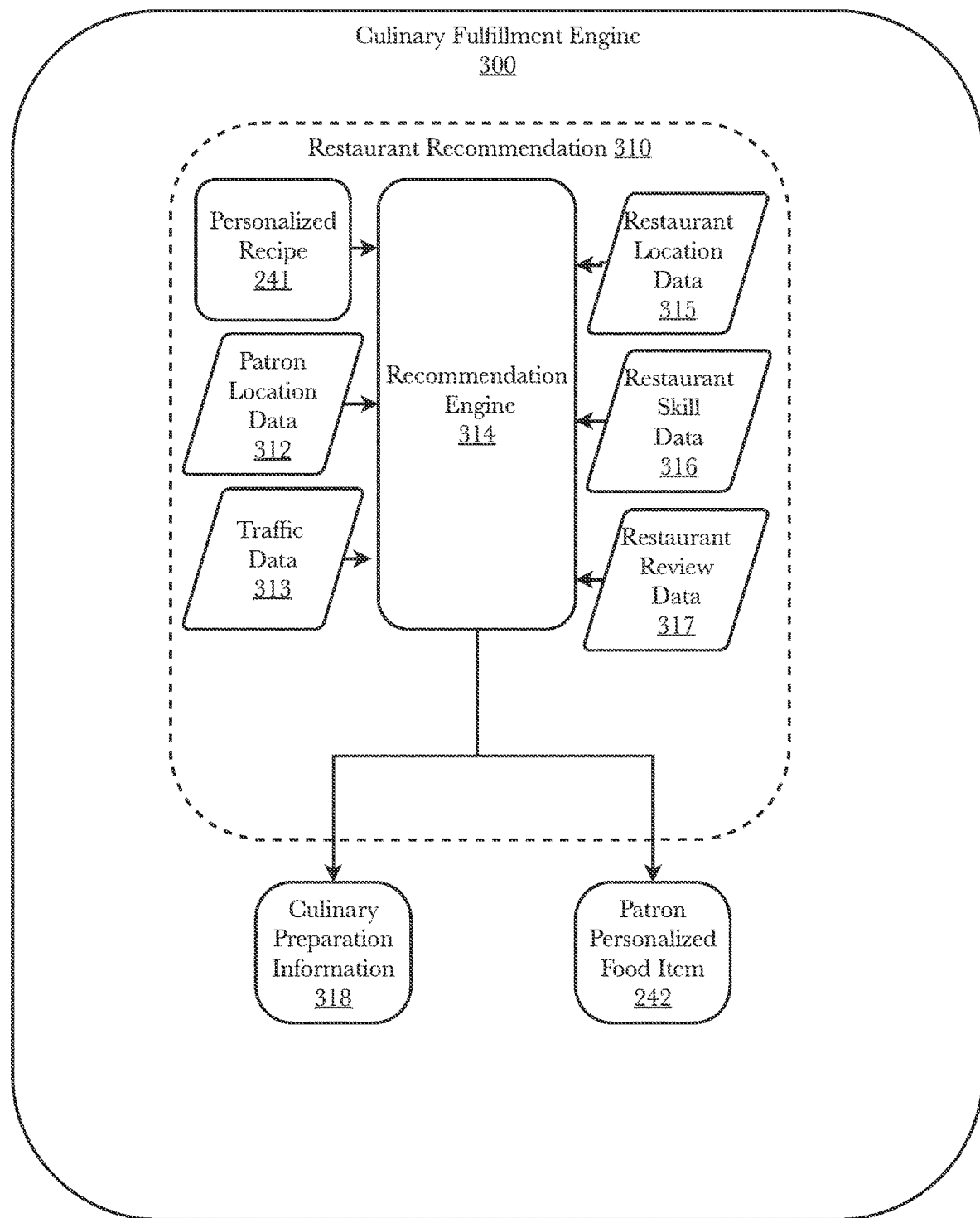
FIG. 3 is a block diagram illustrating an exemplary architecture for an aspect of an automated culinary fulfilment engine.

FIG. 3 is a block diagram illustrating an exemplary architecture for an aspect of an automated culinary fulfilment engine. According to an aspect, culinary fulfilment engine 300 comprises, a restaurant recommendation system 310, comprising a personalized recipe information 241, patron location data 312, traffic data 313, a recommendation engine 314, restaurant location data 315, restaurant skill data 316, restaurant review data 317, culinary preparation information 318, and patron personalized food item 242.

In operation, recommendation engine 314 will take as inputs a personalized recipe information 241, patron location data 312, traffic data 313, restaurant location data 315, restaurant skill data 316, restaurant review data 317. Using semantic vector space methods familiar to those skilled in the art, the input data is represented as word vector and compared using cosine similarity techniques with the optimized target vector to provide as outputs a culinary preparation information 318 that is used by the restaurant and a patron personalized food item 242 that is displayed to the patron.

Figure 14:
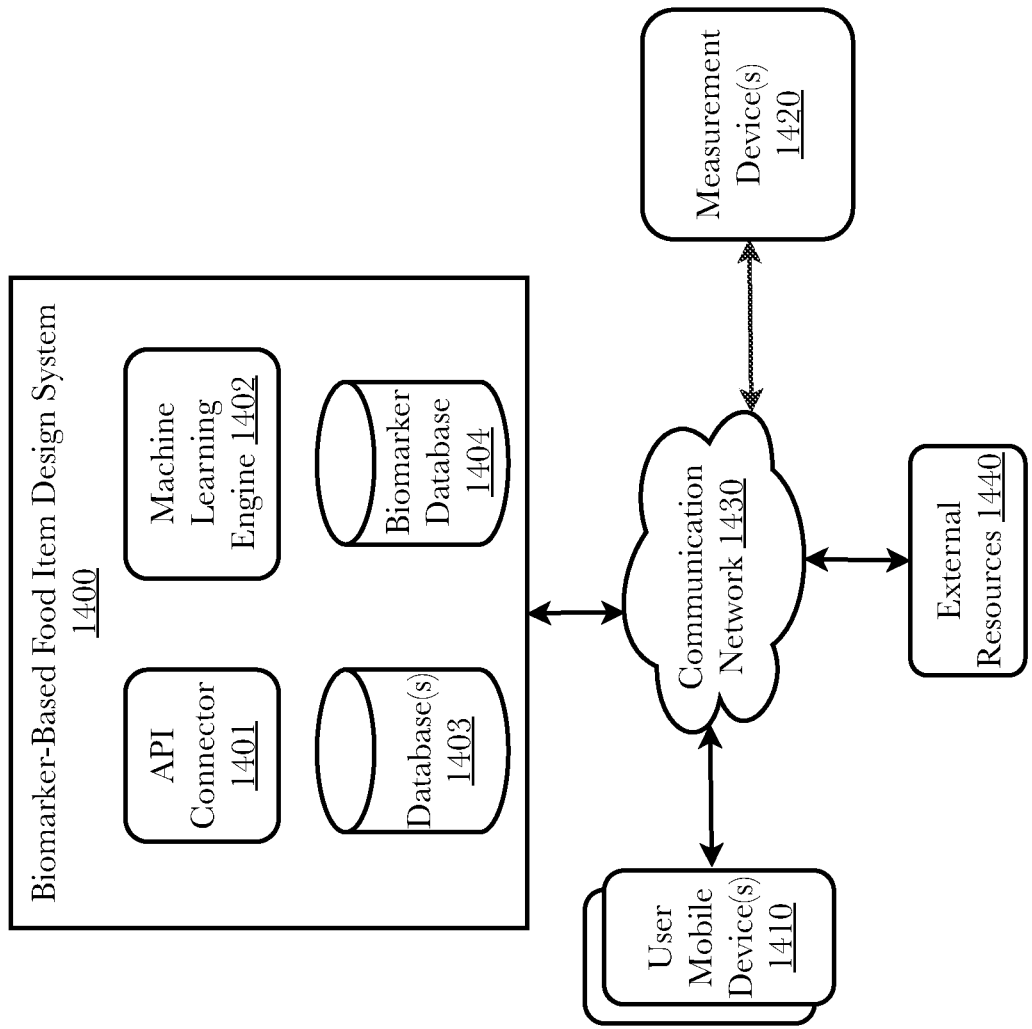
FIG. 14 is a block diagram illustrating an exemplary system architecture for biomarker-based food design, according to an embodiment

FIG. 14 is a block diagram illustrating an exemplary system architecture for biomarker-based food design, according to an embodiment. According to some embodiments, biomarker based food design system 1400 may be configured to connect, via a communication network 1430, to a plurality of measurement devices 1420, user mobile devices 1410, and external resources 1440 in order to ingest a plurality of data related to user preferences, user biomarker data, food item information, and restaurant data in order to train one or more machine learning algorithms (also referred to as machine learning models) operating in a machine learning engine 1402 to identify associations among input data and output a biomarker-based personalized food item recommendation. Biomarker based food design system 1400 may further comprise a machine learning engine 1402 configured to receive training data, input the training data into one or more machine learning algorithms to train a machine learning model that can generate personalized food item recommendations based on biomarker data associated with a user, and deploy the trained machine learning model to generate outputs responsive to new data. System 1400 may also implement an application programming interface (API) connector 1401 configured to identify the appropriate API to initiate data transfer between connected measurement devices 1420 and user mobile devices 1410. Data obtained from the devices 1410, 1420 may be stored in databases(s) 1403, 1404. In some embodiments, some of the data obtained may be compiled into one or more training datasets and stored in database(s) 1403, 1404, until the training datasets may be used as an input to train one or more machine learning algorithms.

According to some embodiments, a plurality of devices 1410, 1420 may be present that can connect to system 1400 via network 1430 in order to engage in bi-directional communication and data exchange. API connector 1401 may be configured to use a plurality of APIs and their associated protocols in order to facilitate data exchange. For example, API connector 1401 may expose and initiate a RESTful (Representational State Transfer) API that uses REST design principles and protocols to request data from a device such as a smart watch (or other smart wearable device) in order to receive from the smart watch various biomarker data associated with the individual wearing the smart watch. In some embodiments, devices 1410, 1420 may include biomarker monitoring devices which can include sensors embedded in smartphones, wearable technologies (e.g., wrist bands, skin patches, etc.), or everyday objects (e.g., smart cap bottles, smart refrigerators, smart weight scales, etc.) that can collect biological, physiological, or behavioral user data, continuously, remotely, and unobtrusively. Such devices may be configured to transmit dense, real-time streams of data and user/biomarker outcomes to system 1400. In some embodiments, user outcomes may refer to biological, physiological, and/or behavioral changes/responses (if any) to items consumed by the user. In some embodiments, user outcomes may comprise biometric (e.g., biological, physiological, and/or behavioral) data responsive to food items consumed by the user of device 1420. In further embodiments, the food items consumed may comprise the non-limiting examples of food obtained from a restaurant (e.g., dine-in, take-out, or delivery), pre-packaged food (e.g., store bought items, etc.), and homemade food (e.g., food prepared at home by device 1410, 1420 user or some other person).

According to some embodiments, a plurality of databases(s) 1403 may be present that may be configured to store a plurality of information related to system 1400 users (e.g., user profile, patron profile, etc.) and their associated measurement device(s) 1420, and restaurant information. Database(s) 1403 may be configured as a user database comprising a plurality of user profiles and for each user profile a set of user preferences, user food item reviews, and historical user biomarker data. Restaurant information may include, but is not limited to, restaurant location data, hours of operation, restaurant website and/or email address, restaurant recipe data, restaurant ingredient data (e.g., nutritional information, ingredient substitution lists, etc.), restaurant skill data, restaurant review data, point-of-sale (POS) data, food and non-food (e.g., plates, napkins, cutlery, etc.) inventory data, restaurant staff schedule data, and the like. In some embodiments, restaurant data and/or user/patron information may be obtained from database(s) 150 of the food item design system 110. In some embodiments, restaurant data and/or user/patron information may alternatively, or redundantly, be obtained from restaurant portal 140 and patron portal 120 respectively.

Also present in some embodiments is a biomarker database 1404 that may be configured to store biomarker data received, retrieved, or otherwise obtained from measurement device(s) 1420 and/or user mobile devices 1410. Examples of biomarkers that may be obtained and stored in biomarker database 1403 can include the non-limiting list of cortisol, blood glucose, blood pressure, testosterone, estrogen, heart rate, blood lead levels, urinalysis, genomics, plasma, serum, cerebrospinal fluid, body temperature, cholesterol, and the like.

As an example of a use case, a system 1400 user may provide a plurality of user biomarker data from either, or both of, measurement device 1420 and user mobile device 1410, and a user specified goal such as, for example, maintain current blood glucose level, to system 1400 which can use the plurality of biomarker data and the user specified goal as inputs into a machine learning model which generates as output a recommended food item which can help the user achieve his or her goal.

Figure 15:
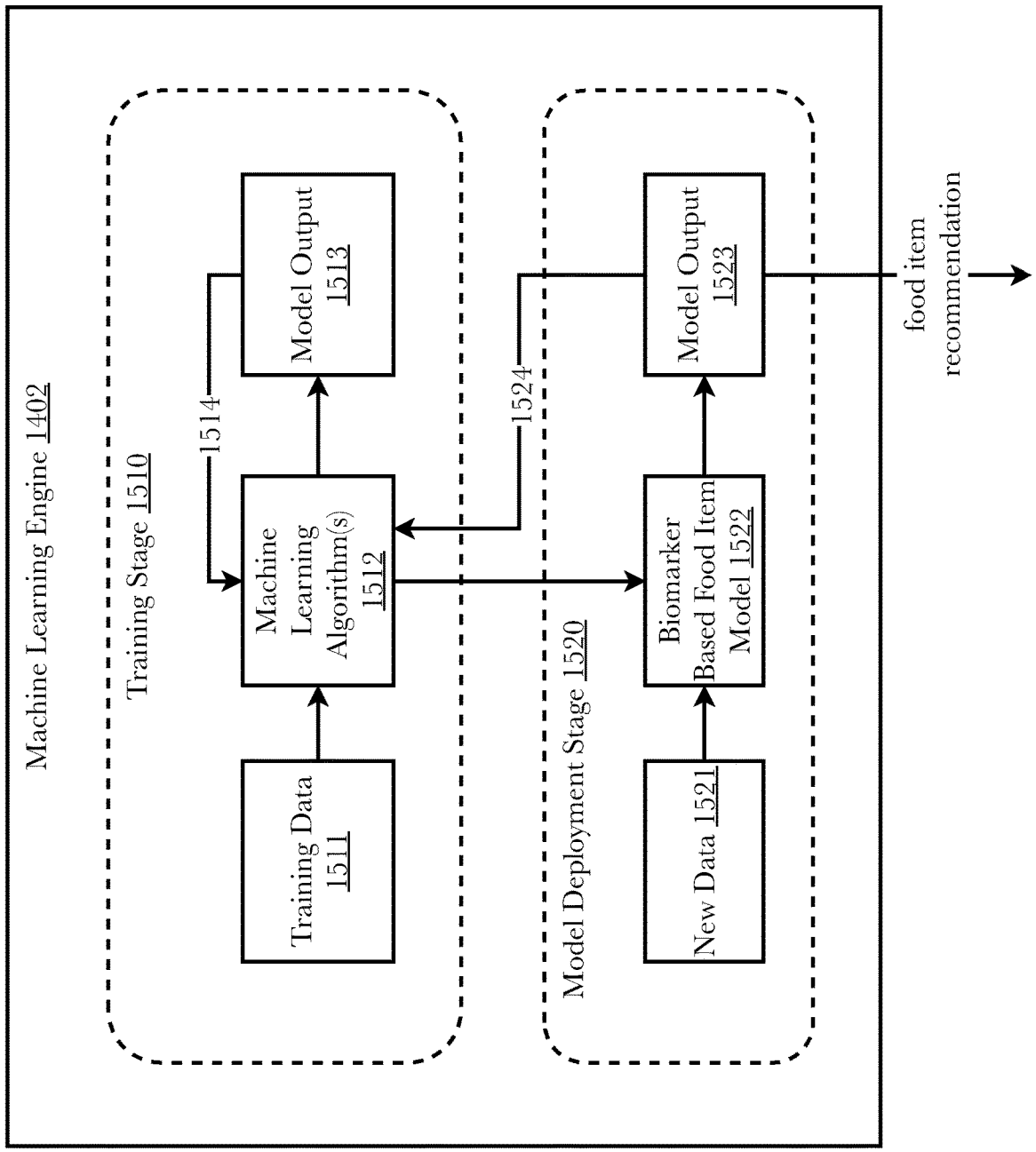
FIG. 15 is a block diagram illustrating an exemplary aspect of system for biomarker-based food design, the machine learning engine.

FIG. 15 is a block diagram illustrating an exemplary aspect of system for biomarker-based food design, the machine learning engine 1402. According to some embodiments, machine learning engine 1402 may comprise a training stage 1510 with one or more machine learning algorithms 1512 which use received, retrieved, or otherwise obtained training data 1511 in order to create one or more biomarker-based food item models 1522. During the training stage 1510 various data may be obtained from a plurality of sources including, but not limited to, measurement devices 1420, mobile devices 1410, databases 1403, 1404, and external resources 1440 such as, for example, third-party data applications and/or services, public and/or private databases, and social media servers. For example, biomarker-based food design system 1400 may obtain biomedical (or other) data from publicly available sources such as PubMed in order to collect information related biomarkers and nutrients/ingredients. In some embodiments, training data may comprise a first biomarker reading to gather baseline biomarker data about a user, a food item or items consumed by the user, and a biomarker reading after the food items have been consumed to gather data about the effects of the food item(s) on the measured biomarker data.

Machine learning engine 1402 may be configured to receive training data from a plurality of users. According to some embodiments, a plurality of user data may be aggregated into one or more training datasets used to train one or more machine learning algorithms 1512 to create a general model. In other embodiments, data received from a single user may be used to create a training dataset used to train one or more machine learning algorithms 1512 to create a user specific model. In other embodiments, a general model may be used as a baseline model to create a user specific model using the user's associated data. During the training stage 1510 the model output 1513 may be implemented and the biomarker response to the implementation may be used as feedback input 1514 to the one or more machine learning algorithms 1512 in order to improve the algorithms' efficiency and fitness. During the feedback 1514 process, model parameter and hyperparameter tuning may take place, further improving the overall utility of the machine learning algorithms 1512 to create useful models to be deployed during runtime.

Once the one or more machine learning algorithms 1512 have been fully trained and machine learning model 1522 is created, the model is ready for the deployment stage 1520 where it may be used with new data 1521 in order to generate model output 1523 such as recommended food items. New data 1521 may comprise real-time biomarker data streams, nutritional information associated with ingredients and food items, recipes, user specified food goals, user preferences, and the like. New data 1521 may be received from measurement devices 1420, user mobile devices 1410, databases 1403, 1404, and external resources 1440. Model outputs and biomarker data obtained after a user has consumed a recommended food item may be used as feedback data 1524 to be used as training input to the one or more machine learning algorithms in the training stage 1510. In this way, machine learning algorithms 1512 and the machine learning model 1522 may continuously learn and become better at making predictions.

According to some embodiments, machine learning engine 1402 may be configured to use any desirable machine learning techniques to learn or train biomarker-based food item model(s) 1522 using training data 1511. Examples of machine learning techniques that can be used include, but are not limited to, supervised learning based techniques (e.g., artificial neural networks, Bayesian-based techniques, decision trees, etc.), unsupervised learning based techniques (e.g., data clustering, expectation-maximization algorithms, etc.) reinforcement learning based techniques, deep learning based techniques, and the like. As a more specific example of a type of machine learning technique that may be used by machine learning engine 1402, consider the use the unsupervised machine learning technique to produce a neural network that can receive as inputs a plurality of biomarker data, nutritional information for a plurality of food items and their ingredients, and a user specified biomarker goal, and generates as outputs a recommended food item that can help achieve the user specified biomarker goal. As another example, machine learning engine 1402 algorithms may convert the input data (e.g., biomarker data, food item information, user preferences, recipes, nutritional information, restaurant information, etc.) into a set of vector representations, which can be fed into the one or more machine learning algorithms 1512 to identify associations among the input data, convert a user specified biomarker goal into a second set of vector representations, and then pass the second set of vectors through the one or more machine learning algorithms to obtain a best fit between the user specified biomarker goal and the identified associations. In this scenario, according to some embodiments, the best fit may comprise a recommended food item which can be consumed by the user to help achieve the user specified goal. According to some embodiments, food item recommendations may be sent back to the user mobile device 1410.

As an additional example, consider the use case of a diabetic user who has the goal of "maintain blood glucose levels" so that the user is able to eat a slice of birthday cake at a relative's birthday party. Machine learning engine 1402 may receive the user's current biomarker data and the goal and then generate a food item recommendation that allows the user to eat a meal and eat cake without his or her blood sugar levels going up. The system 1400 may be configured to continuously measure glucose levels in the blood as the user orders and consumes food, which can result in the system recommending the right plates (food items) to people with diabetes.

Detailed Description of Exemplary Aspects

Figure 4:
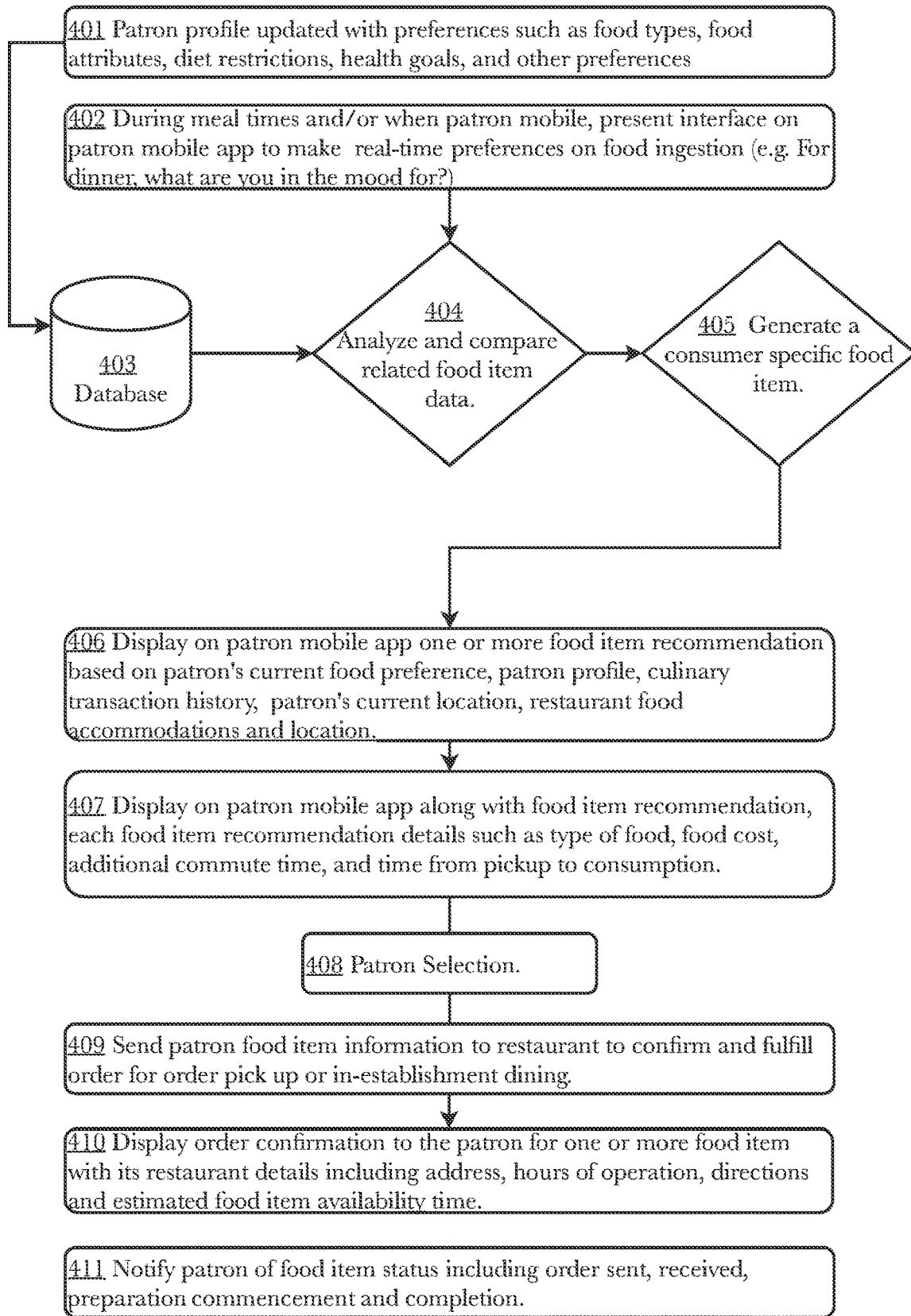
FIG. 4 is a flow diagram showing the steps of an exemplary method for personalized food item design, selection, restaurant selection, order fulfilment and receipt by a restaurant patron.

FIG. 4 is a flow diagram showing the steps of an exemplary method for personalized food item design, selection, restaurant selection, order fulfilment by selected restaurant. A patron portal is provided for the patron to pre-enter preferences such as food types, food attributes, diet restrictions, health goals, and other preferences 401 this information is subsequently stored in a historical database 403 for future use. During mealtime and/or when patron is mobile, the patron is presented with an interface on mobile app to make real-time preferences on meal interests or desires for food ingestion, the app may ask "for dining, what are you in the mood for?" 402. An analysis (as further exemplified in FIG. 5) is performed on patrons historical and real-time food item requirements and compared to menu options and culinary capabilities of restaurants in proximity of patron 404 from which a consumer specific food item is generated 405. The food item options 406 are displayed to the patron, along with a recommended restaurant, with details such as type of food, food cost, additional drive time 407. A choice is made from the patron 408 for one or more food item displayed with its recommended restaurant. The patron's food item information is sent to the restaurant, confirmation to patron and food item fulfilment 409. Display food item confirmation along with restaurant details including restaurant address, driving, estimated travel time and estimated food item availability 410. Notify and update patron on order status and restaurant fulfilment 411.

FIG. 5 is a flow diagram showing the steps of an exemplary method for an optimized food item recommendation to a particular restaurant patron based upon their preferences and patron profile. Convert patron food item text documents to corresponding word vector 501. Convert restaurant recipe, restaurant ingredient data and culinary preparation skill text documents to corresponding word vectors 502. Using a matrix dimension reduction technique such as principal dimension analysis or others known to those skilled in the art, reduce the input matrix for more effective processing. Compare resultant vectors using semantic term vector space techniques known to one in the art 503. Select restaurant word vector that is most similar to the patron food item requirement 504. Modify restaurant recipe items based on restaurant ingredients, culinary capabilities to most closely align to patron's requirements 505. Output food item description and recipe to patron and restaurant 506.

Figure 6:
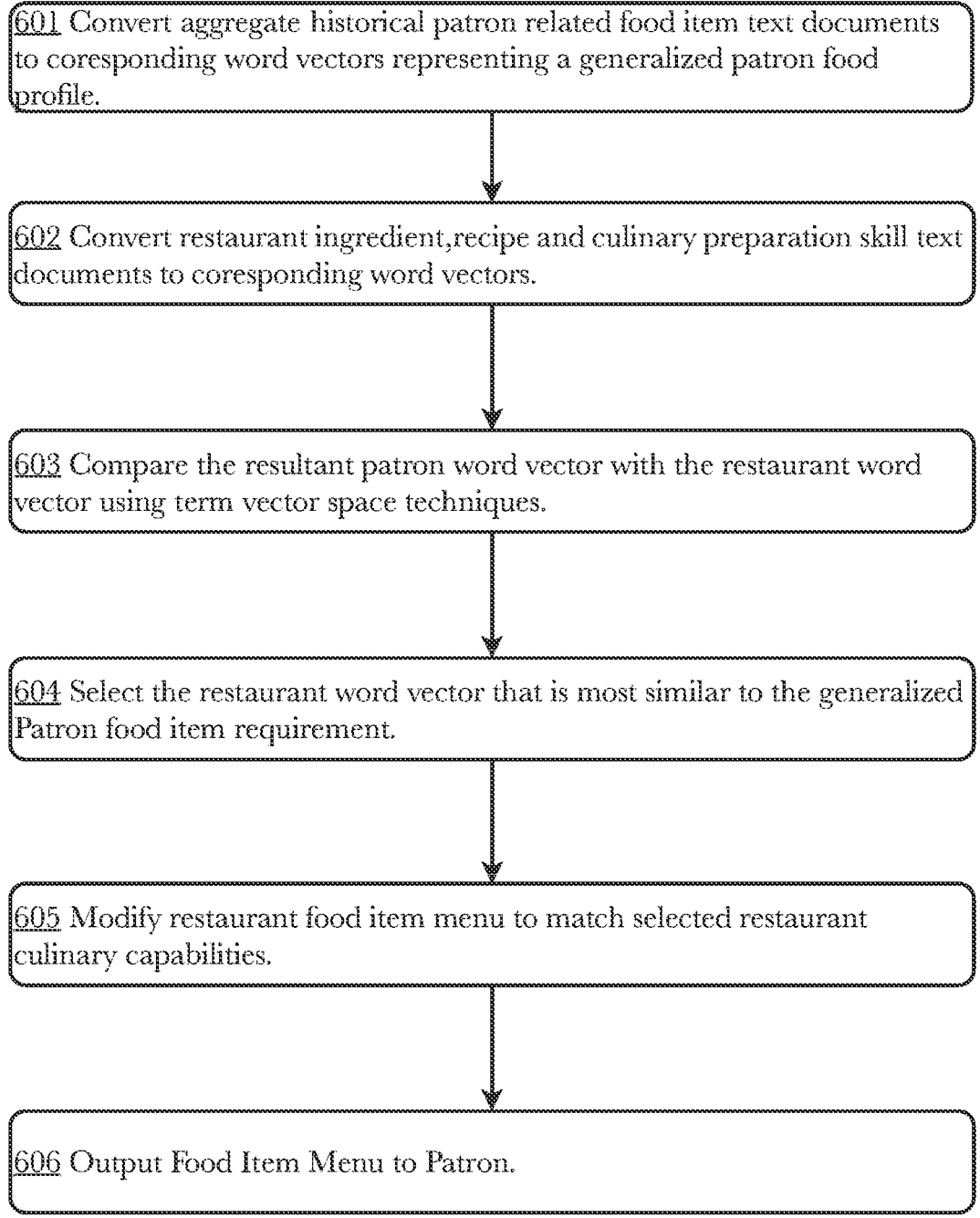
FIG. 6 is a flow diagram showing the steps of an exemplary method for an optimized food item recipe generation process based on the restaurants' food ingredients on hand, culinary skills and a predicted patron preference.

FIG. 6 is a flow diagram showing the steps of an exemplary method for an optimized food item based on the restaurants' food ingredients on hand, culinary skills and a predicted preference of a patron. Convert aggregate historical patron food item text documents to corresponding word vectors to represent generalized patron food profile 601. Convert restaurant recipe and culinary preparation text documents to corresponding word vectors 602. Compare resultant vectors using term vector space techniques 603. Select restaurant word vector that is most similar to the generalized patron food item requirement 604. Modify restaurant recipe items based on restaurant ingredients, culinary capabilities to most closely align to generic patron's requirements 605. Output food item menu to patron 606.

An exemplary semantic comparison method may include term vector space analysis technique to those familiar in the art. Term vector modeling is an algebraic model for representing text and text documents as vectors. Each term or word in a text document typically corresponds to a dimension in that vector. Once a text document is described as a word vector, comparisons between two vectors may be made using vector calculus. One useful technique to determine similarities between documents is by comparing the deviation of angles between each document vector and the original query vector where the query is represented as a vector with same dimension as the vectors that represent the other documents.

An exemplary dimensional reduction technique familiar to those skilled in the art is Principal Component Analysis ("PCA"), which may be used to optimize the variables prior to vectorization to reduce dimensionality of resulting vectors prior to feeding into a machine learning algorithm.

An exemplary recipe optimization method may include deep learning techniques familiar to those skilled in the art. One such form of deep learning that is particularly useful when generating text is Recurrent Neural Networks ("RNN") using long short-term memory ("LSTMs") units or cells. A single LS™ is comprised of a memory-containing cell, an input gate, an output gate and a forget gate. The input and forget gate determine how much of incoming values transit to the output gate and the activation function of the gates is usually a logistic function. The initial input data will cause the model to learn the weights of connections that influence the activity of these gates which will impact the resultant output. To generate unique personalized recipes for a given patron, standard recipes along with the patron profile data are fed into the input gate of the RNN, in turn the RNN will learn what's important to the patron and create unique recipe outputs.

Figure 11:
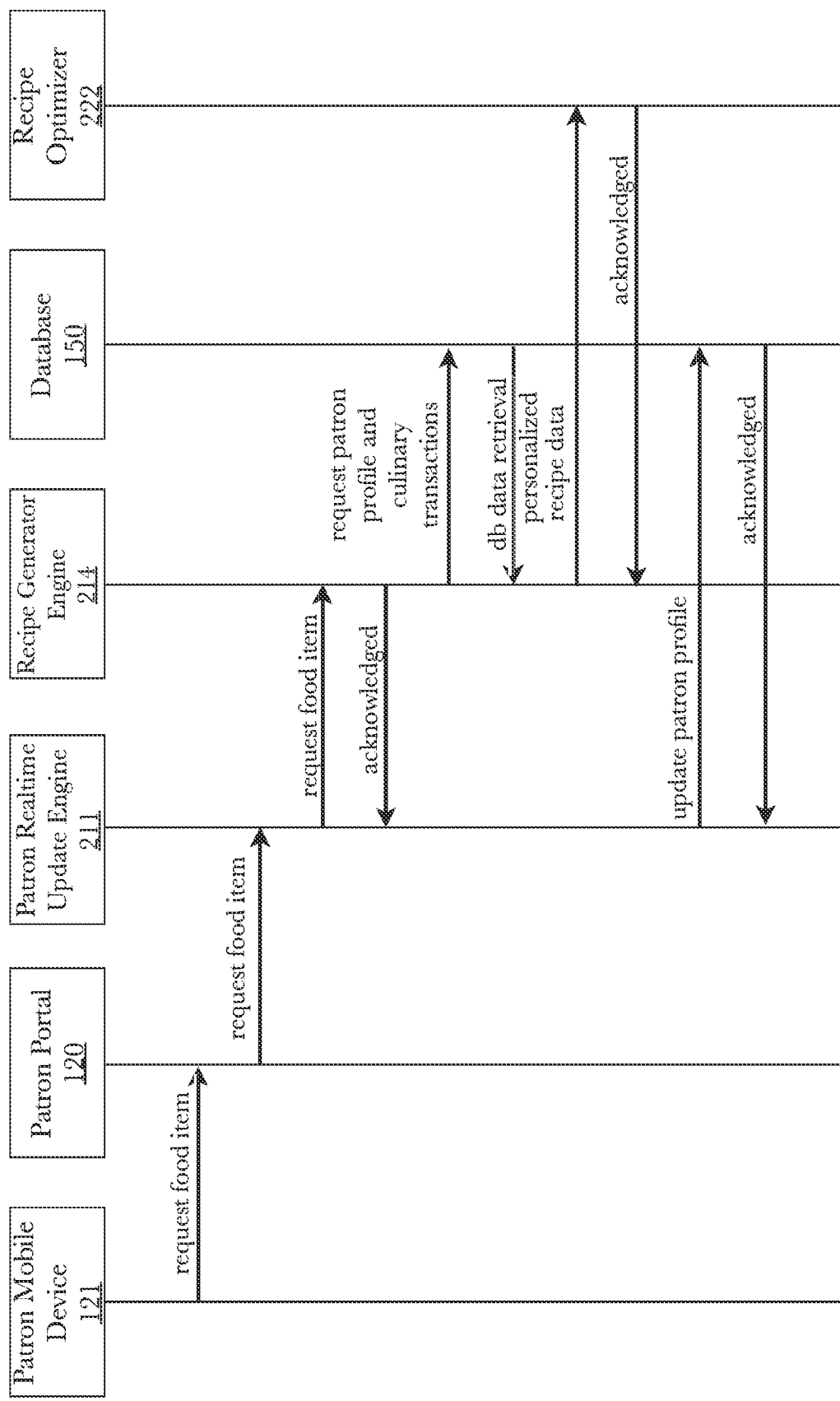
FIG. 11 is a message diagram showing exemplary messaging between patron device and recipe generation system with output to the recipe optimization system.

FIG. 11 is a message diagram showing exemplary messaging between patron device 110 and recipe generation system with output to the recipe optimizer 222. Initially, a patron device 110 connects to a patron portal 120 to submit a food item request. The request may then be relayed by the patron portal 120 to a patron realtime update engine 211, which then relays the request to a recipe generator engine 214 and updates the patron's profile in a database 150. Recipe generator engine 214 acknowledges the request and retrieves stored patron profile and previous culinary transactions from the database 150, and uses this information to generate personalized recipe data for the specific patron that is then sent to the recipe optimizer 222.

Figure 12:
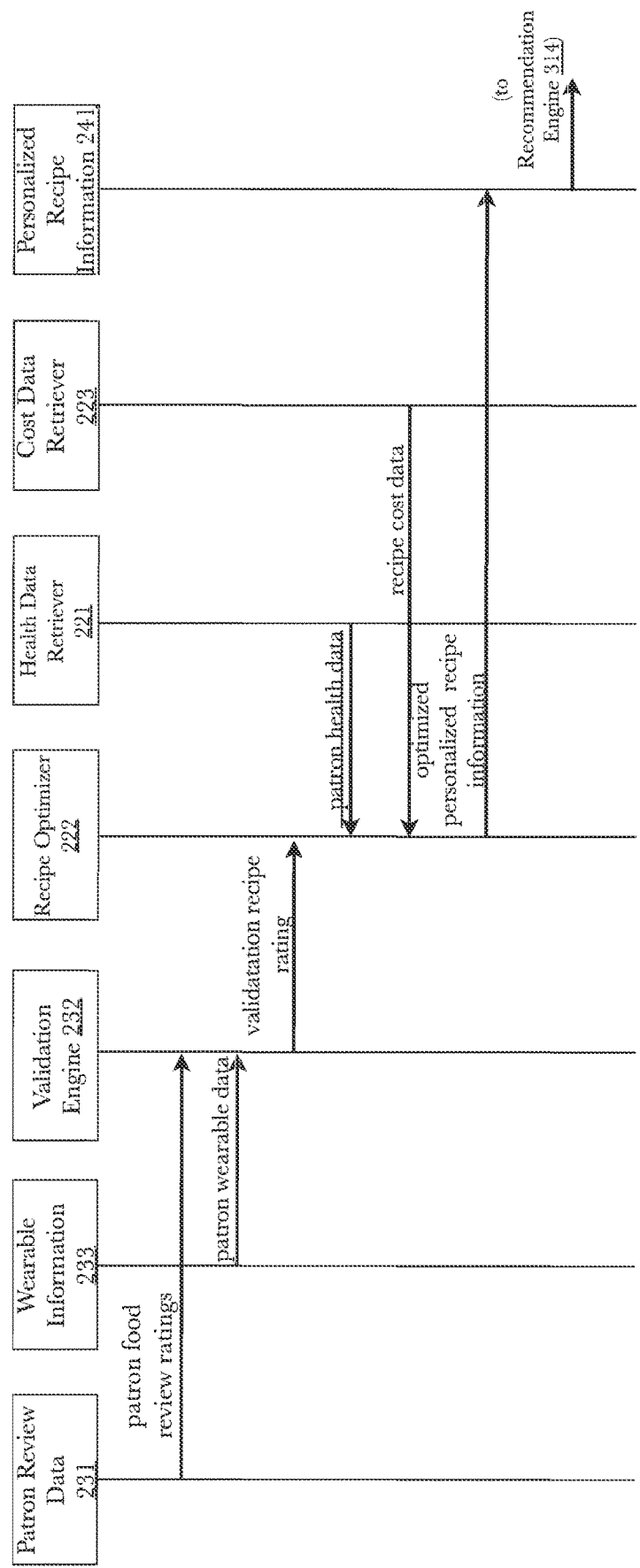
FIG. 12 is a message diagram showing exemplary messaging within the recipe optimization system taking inputs from a recipe generation system and a recipe validation system and providing an optimized personalized recipe information as an output to restaurant recommendation system.

FIG. 12 is a message diagram showing exemplary messaging within the recipe optimization system taking inputs from a recipe generation system and a recipe validation system and providing an optimized personalized recipe information as an output to restaurant recommendation system. Patron review data 231, submitted by patrons, and patron wearable data 233, transmitted by wearable devices patrons may be wearing, are received at a validation engine 232. Validation engine 232 uses this information to produce a validated recipe rating that is sent to a recipe optimizer 222, which then retrieves patron health data and cost data associated with the recipe (for example, ingredient costs and prep times) using health data retriever 221 and cost data retriever 223, respectively. This information is used to further adjust the recipe and produce personalized recipe information 241, which is then sent as output to a recommendation engine 314.

Figure 13:
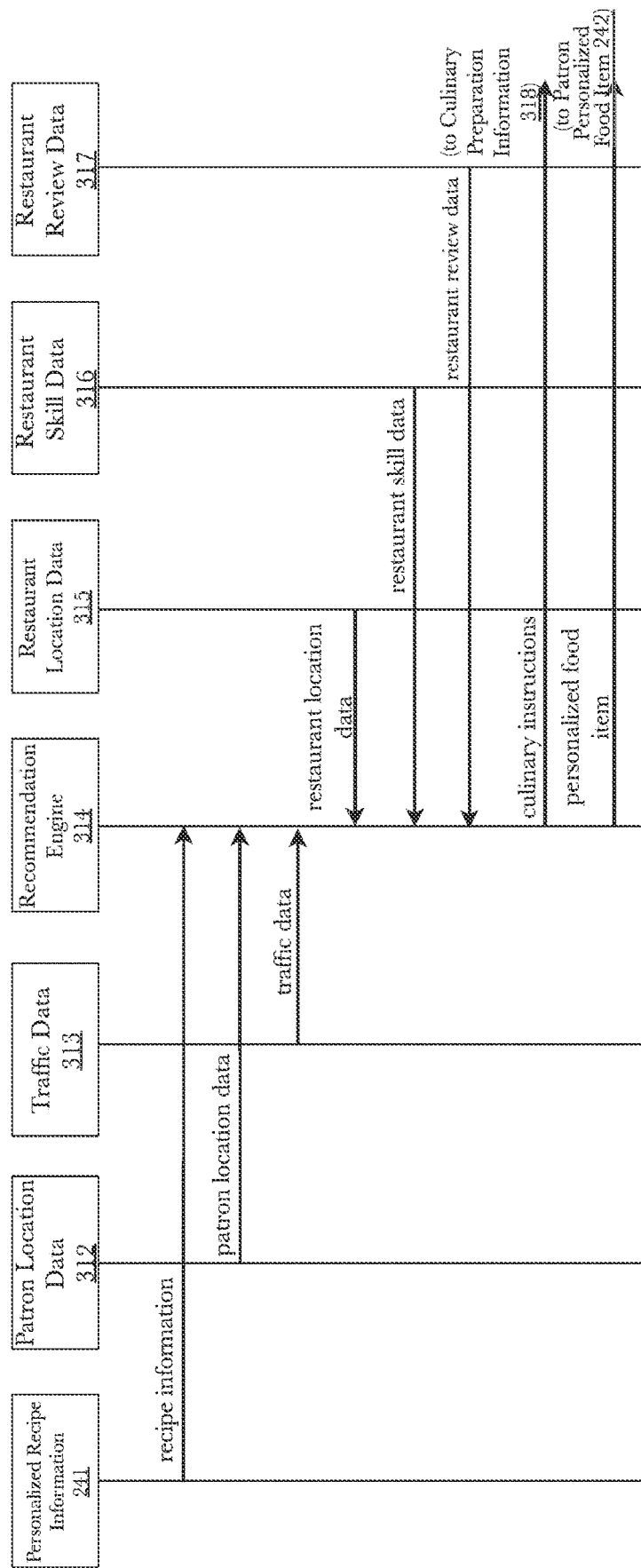
FIG. 13 is a message diagram showing exemplary messaging within a restaurant recommendation system with various inputs and providing culinary preparation and personalized food item output information.

FIG. 13 is a message diagram showing exemplary messaging within a restaurant recommendation system with various inputs and providing culinary preparation and personalized food item output information. Personalized recipe information 241 is received at a recommendation engine 314 from a recipe optimizer 222, as described above (with reference to FIG. 12). Recommendation engine 314 also receives information from a number of sources to assist with producing a specific recipe recommendation, including (but not limited to) patron location data 312, traffic data 313, restaurant location data 315, restaurant skill data 316 (such as the skills of individual chefs that are working at the time), and restaurant review data 317. This aggregated information may then be used to produce a patron-specific personalized food item 242, along with a set of culinary instructions for preparing the patron-specific item that may be sent as culinary preparation information 318.

Figure 16:
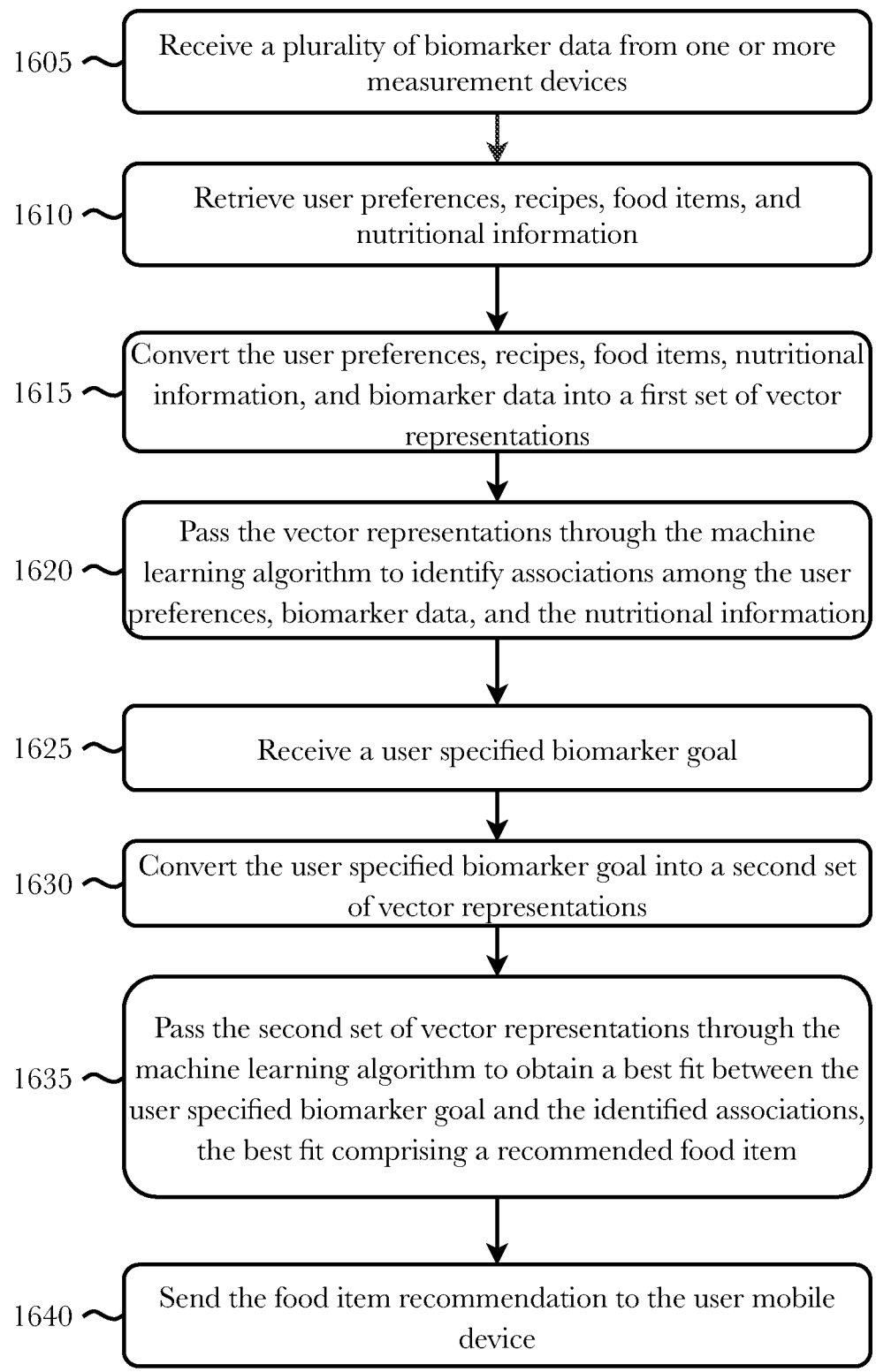
FIG. 16 is a flow diagram illustrating an exemplary method for generating personalized, biomarker-based food item recommendations, according to an embodiment.

FIG. 16 is a flow diagram illustrating an exemplary method for generating personalized, biomarker-based food item recommendations, according to an embodiment. According to an embodiment, the process begins at step 1605 when machine learning engine 1402 receives a plurality of biomarker data associated with a user from one or more measurement devices 1420 and/or user mobile devices 1410. As a next step 1610, machine learning engine 1402 may retrieve user preferences, recipes, food items, and nutritional information from database(s) 1403, 1404 and then convert the user preferences, recipes, food items, nutritional information, and biomarker data into a first set of vector representations at step 1615. As a next step 1620, the vector representations may be passed through the one or more machine learning algorithms 1512 to identify associations among the user preferences, biomarker data, and nutritional information. Machine learning engine 1402 may receive a user specified biomarker goal at step 1625 and then convert the user specified biomarker goal into a second set of vector representations at step 1630. Once converted, the second set of vector representations may be passed through the machine learning algorithm 1512 to obtain a best fit between the user specified biomarker goal and the identified associations at step 1635. As a last step 1640, the recommended food item may be sent to the user via their mobile device 1410. In this way, the biomarker-based food item design system 1400 can generate personalized food item recommendations based on current user biomarker levels, a user specified biomarker goal, and nutritional information associated with available ingredients and food items.

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the aspects disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific aspects, at least some of the features or functionalities of the various aspects disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some aspects, at least some of the features or functionalities of the various aspects disclosed herein may be implemented in one or more virtualized computing environments (e.g., network computing clouds, virtual machines hosted on one or more physical computing machines, or other appropriate virtual environments).

Figure 7:
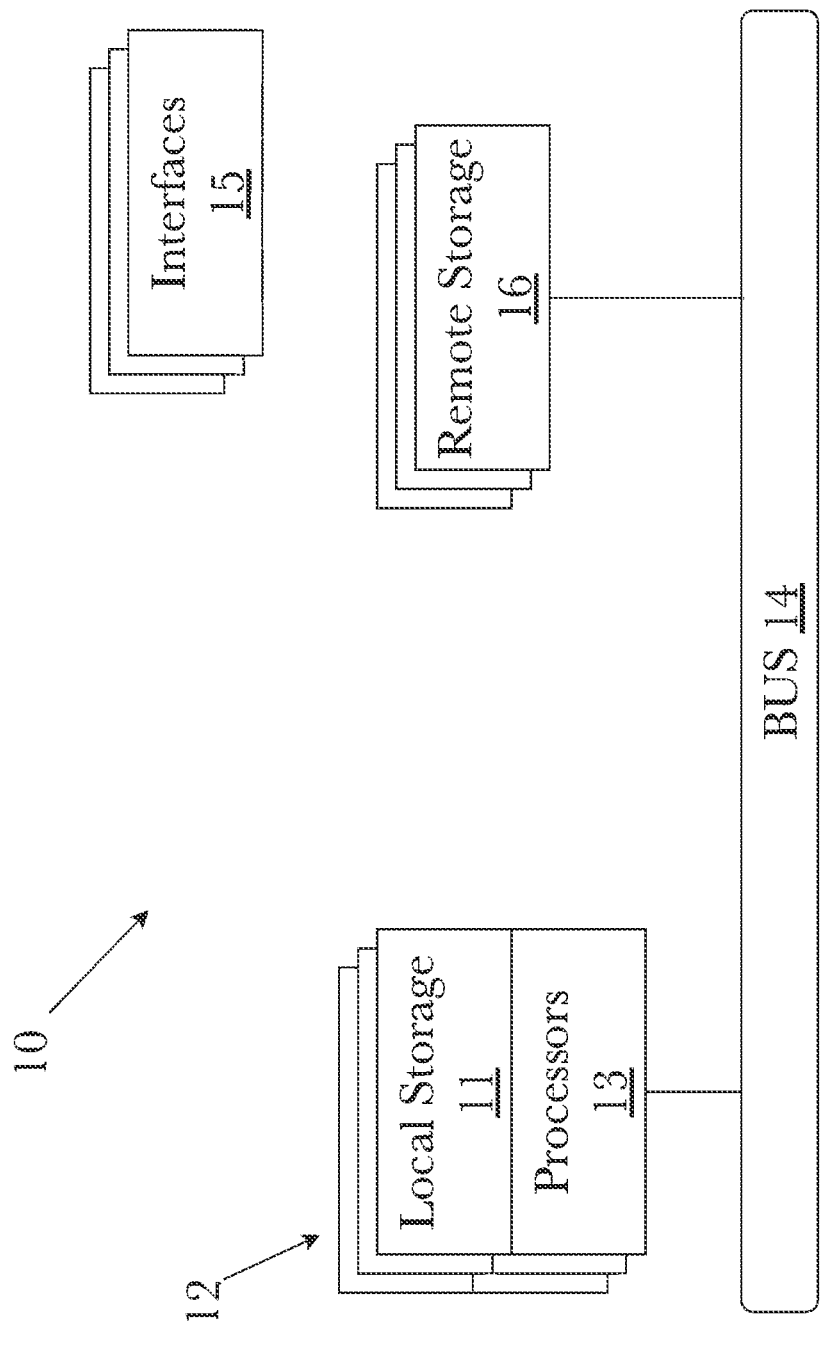
FIG. 7 is a block diagram illustrating an exemplary hardware architecture of a computing device.

Referring now to FIG. 7, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one aspect, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one aspect, a computing device 10 may be configured or designed to function as a server system utilizing CPU 12, local memory 11 and/or remote memory 16, and interface(s) 15. In at least one aspect, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some aspects, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11 (such as non-volatile random access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (Wi-Fi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 7 illustrates one specific architecture for a computing device 10 for implementing one or more of the aspects described herein, it is by no means the only device architecture on which at least a portion of the features and techniques described herein may be implemented. For example, architectures having one or any number of processors 13 may be used, and such processors 13 may be present in a single device or distributed among any number of devices. In one aspect, a single processor 13 handles communications as well as routing computations, while in other aspects a separate dedicated communications processor may be provided. In various aspects, different types of features or functionalities may be implemented in a system according to the aspect that includes a client device (such as a tablet device or smartphone running client software) and server systems (such as a server system described in more detail below).

Regardless of network device configuration, the system of an aspect may employ one or more memories or memory modules (such as, for example, remote memory block 16 and local memory 11) configured to store data, program instructions for the general-purpose network operations, or other information relating to the functionality of the aspects described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device aspects may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

Figure 8:
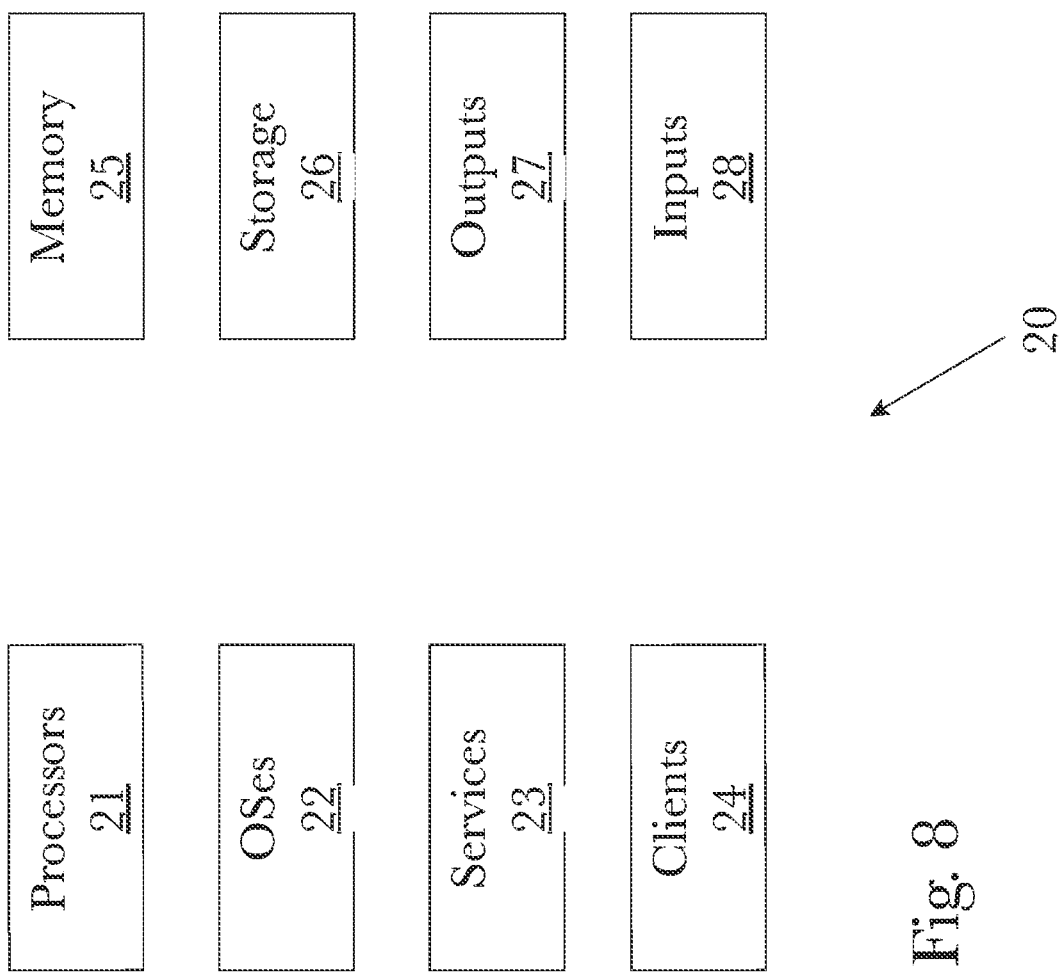
FIG. 8 is a block diagram illustrating an exemplary logical architecture for a client device.

In some aspects, systems may be implemented on a standalone computing system. Referring now to FIG. 8, there is shown a block diagram depicting a typical exemplary architecture of one or more aspects or components thereof on a standalone computing system. Computing device 20 includes processors 21 that may run software that carry out one or more functions or applications of aspects, such as for example a client application 24. Processors 21 may carry out computing instructions under control of an operating system 22 such as, for example, a version of MICROSOFT WINDOWS™ operating system, APPLE macOS™ or iOS™ operating systems, some variety of the Linux operating system, ANDROID™ operating system, or the like. In many cases, one or more shared services 23 may be operable in system 20 and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 8). Examples of storage devices 26 include flash memory, magnetic hard drive, CD-ROM, and/or the like.

Figure 9:
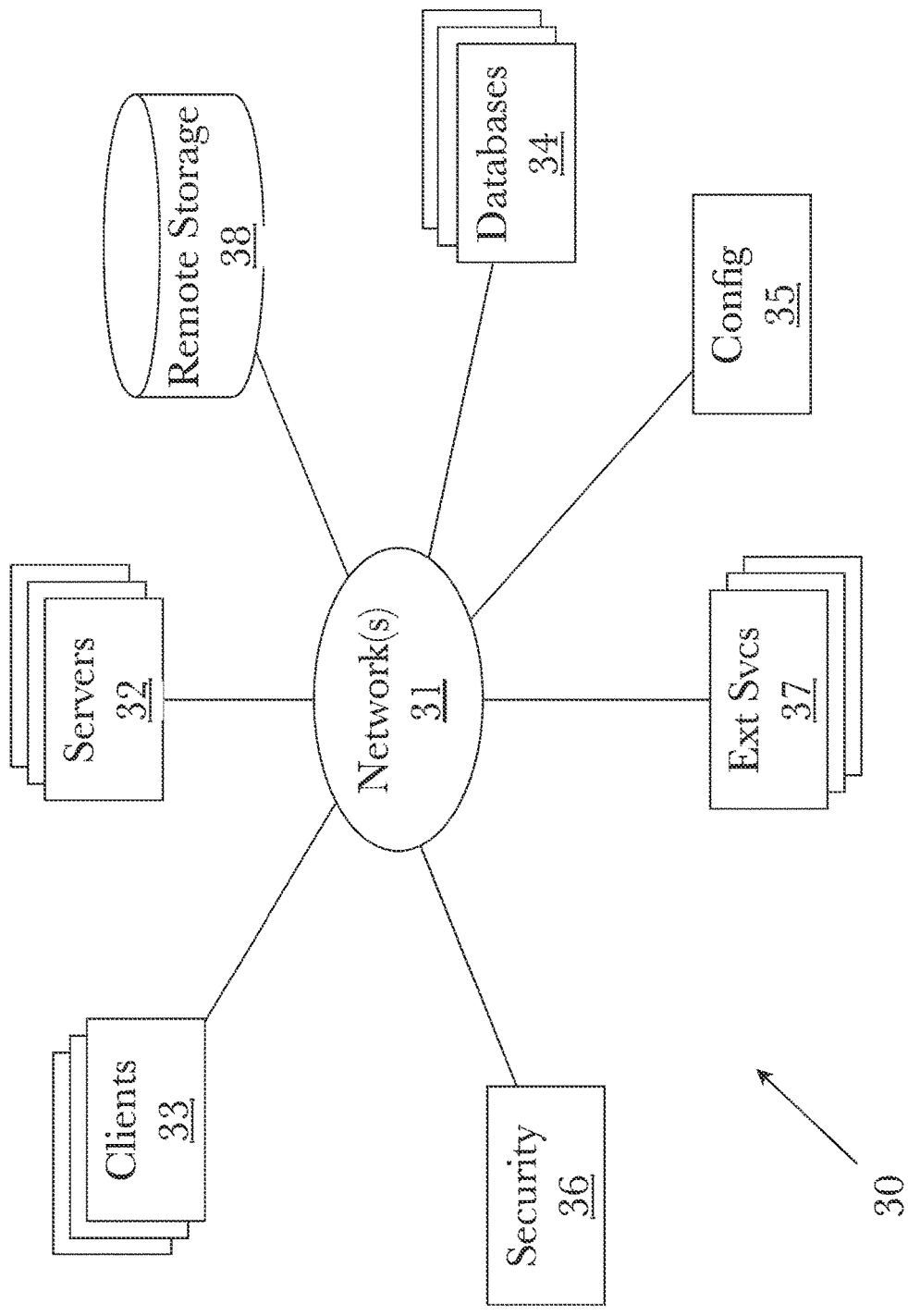
FIG. 9 is a block diagram showing an exemplary architectural arrangement of clients, servers, and external services.

In some aspects, systems may be implemented on a distributed computing network, such as one having any number of clients and/or servers. Referring now to FIG. 9, there is shown a block diagram depicting an exemplary architecture 30 for implementing at least a portion of a system according to one aspect on a distributed computing network. According to the aspect, any number of clients 33 may be provided. Each client 33 may run software for implementing client-side portions of a system; clients may comprise a system 20 such as that illustrated in FIG. 8. In addition, any number of servers 32 may be provided for handling requests received from one or more clients 33. Clients 33 and servers 32 may communicate with one another via one or more electronic networks 31, which may be in various aspects any of the Internet, a wide area network, a mobile telephony network (such as CDMA or GSM cellular networks), a wireless network (such as Wi-Fi, WiMAX, LTE, and so forth), or a local area network (or indeed any network topology known in the art; the aspect does not prefer any one network topology over any other). Networks 31 may be implemented using any known network protocols, including for example wired and/or wireless protocols.

In addition, in some aspects, servers 32 may call external services 37 when needed to obtain additional information, or to refer to additional data concerning a particular call. Communications with external services 37 may take place, for example, via one or more networks 31. In various aspects, external services 37 may comprise web-enabled services or functionality related to or installed on the hardware device itself. For example, in one aspect where client applications 24 are implemented on a smartphone or other electronic device, client applications 24 may obtain information stored in a server system 32 in the cloud or on an external service 37 deployed on one or more of a particular enterprise's or user's premises. In addition to local storage on servers 32, remote storage 38 may be accessible through the network(s) 31.

In some aspects, clients 33 or servers 32 (or both) may make use of one or more specialized services or appliances that may be deployed locally or remotely across one or more networks 31. For example, one or more databases 34 in either local or remote storage 38 may be used or referred to by one or more aspects. It should be understood by one having ordinary skill in the art that databases in storage 34 may be arranged in a wide variety of architectures and using a wide variety of data access and manipulation means. For example, in various aspects one or more databases in storage 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth).

In some aspects, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, some aspects may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with aspects without limitation, unless a specific security 36 or configuration system 35 or approach is specifically required by the description of any specific aspect.

Figure 10:
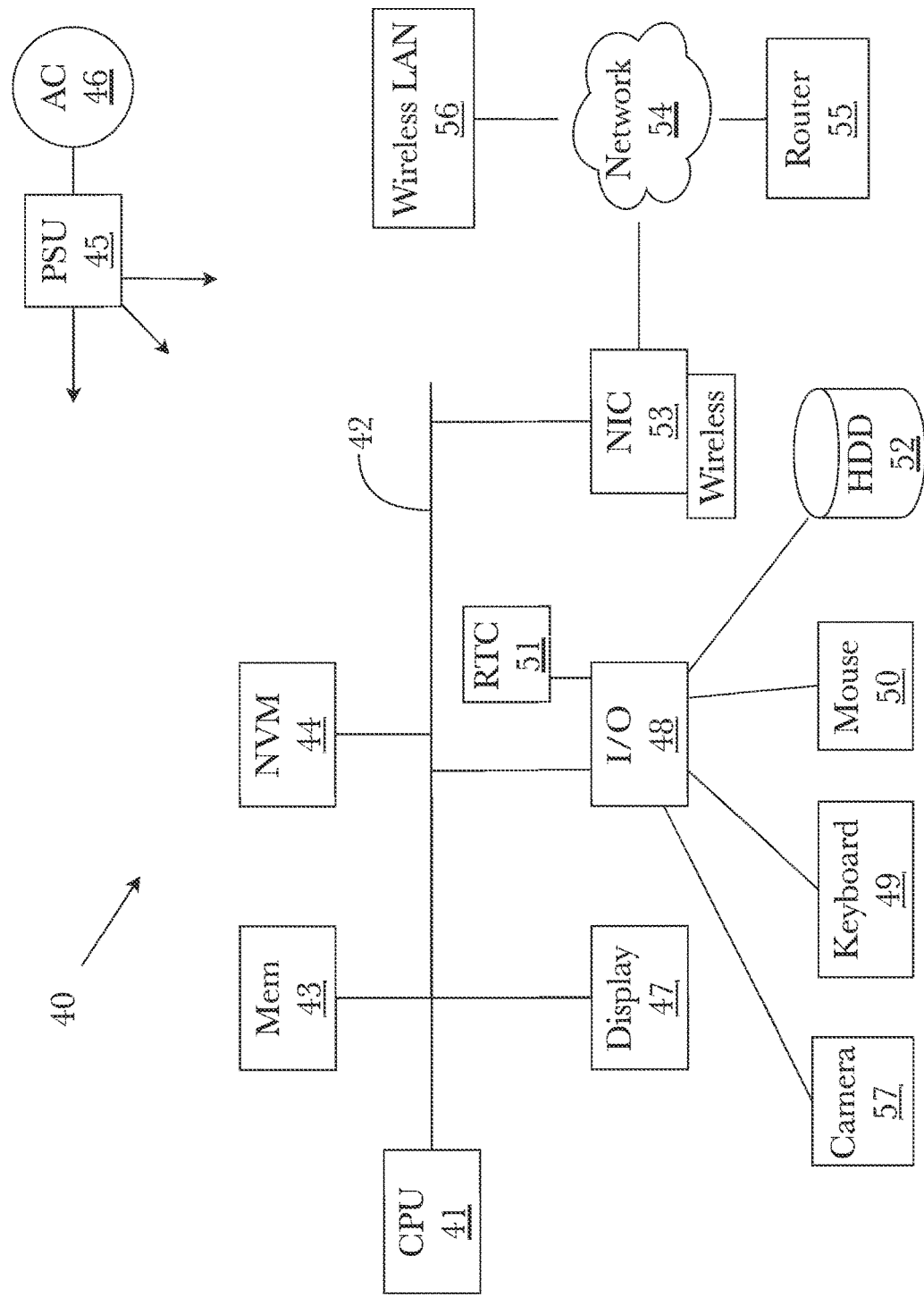
FIG. 10 is block diagram illustrating another aspect of an exemplary hardware architecture of a computing device.

FIG. 10 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to peripherals such as a keyboard 49, pointing device 50, hard disk 52, real-time clock 51, a camera 57, and other peripheral devices. NIC 53 connects to network 54, which may be the Internet or a local network, which local network may or may not have connections to the Internet. The system may be connected to other computing devices through the network via a router 55, wireless local area network 56, or any other network connection. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various aspects, functionality for implementing systems or methods of various aspects may be distributed among any number of client and/or server components. For example, various software modules may be implemented for performing various functions in connection with a system of any particular aspect, and such modules may be variously implemented to run on server and/or client components.

According to an aspect, restaurant menu optimization and experimentation may be performed with a patron who enters a restaurant with a known patron profile. The system may predict and offer highly desirable "chefs specials" that satisfies the patron preferences by making variations of known dishes on the restaurant menu. The "chef's special" are automatically designed by system and may include Artificial Intelligent methods familiar to those skilled in the art.

According to another aspect, restaurant menu optimization and experimentation may be performed with a patron who enters a restaurant with an unknown patron profile. The system may predict and offer highly desirable "chefs specials" that provide A/B experimentation by making variations of known dishes on the restaurant menu and then by tuning the menu to provide an optimal patron menu. The "chef's special" are automatically designed by system and may include Artificial Intelligent methods familiar to those skilled in the art.

According to another aspect, recipe optimization may be performed on multiple patrons at the same time as may be the case for dining parties of two or more at a restaurant. For example, in a party of four seated at the same table, of whom three have profile information available to system, and one with a raspberry allergy and one is gluten intolerant. The system may predict and offer highly desirable "chefs specials" that satisfy each persons preferences amongst those whom food preferences are known while avoiding allergic ingredients for the whole table. The "chef's special" may include Artificial Intelligent methods familiar to those skilled in the art.

According to another aspect, patron wearable devices may provide real-time feedback directly into the food design system. For example, a Continuous Glucose Monitor (GCM) may provide input into the recipe device, and based on patron current glucose level offer additional/different options for a choice of dessert and/or menu options for future meals.

According to another aspect, a home food inventory system may be used as input into a recipe generator to provide food preparation options based on current in home food inventory.

The skilled person will be aware of a range of possible modifications of the various aspects described above. Accordingly, the present invention is defined by the claims and their equivalents.

What is claimed is:

1. A system for biomarker-based personalized food item design, comprising:
    a computing device comprising a memory, a processor, and a non-volatile data storage device;
    a recipe database stored on the non-volatile data storage device, the recipe database comprising a plurality of recipes, each recipe comprising a food type, a list of required ingredients and for each ingredient nutritional information;
    a restaurant database stored on the non-volatile data storage device, the restaurant database comprising a plurality of restaurant locations, each restaurant location further comprising restaurant data comprising:
        a list of available culinary skills; and
        a list of available ingredients;
    a user profile database stored on the non-volatile data storage device, the user profile database comprising a plurality of user profiles, each user profile comprising user preferences;
    a machine learning algorithm configured to identify associations among the user preferences, biomarker data, and the nutritional information;
    a machine learning engine comprising a first plurality of programming instructions stored in the memory of, and operating on the processor of, the computing device, wherein the first plurality of programming instructions, when operating on the processor, causes the computing device to:
        receive, from a measurement device, biomarker data associated with a user of the measurement device;
        convert the user preferences, recipes, food items, nutritional information, restaurant information, and biomarker data into a first set of vector representations;
        pass the vector representations through the machine learning algorithm to identify associations among the user preferences, biomarker data, restaurant information, and the nutritional information, the identified associations comprising a required culinary skill and a list of required ingredients;
        receive, from a user mobile device, a user specified biomarker goal;
        convert the user specified biomarker goal into a second set of vector representations;
        pass the second set of vector representations through the machine learning algorithm to obtain a best fit between the user specified biomarker goal and the identified associations, the best fit comprising a recommended food item and a restaurant having the required culinary skill and the list of required ingredients to prepare the recommended food item; and
        send the food item recommendation and the restaurant recommendation to the user mobile device.

2. The system of claim 1, wherein the biomarker data comprises biological, physiological, and/or behavioral information.

3. The system of claim 1, wherein the measurement devices comprise sensors embedded in the user mobile device and wearable technologies.

4. The system of claim 1, wherein the user preference is based on nutritional data retrieved from a third-party resource over a network.

5. The system of claim 1, wherein the user specified biomarker goal is to regulate biomarker outcomes.

6. The system of claim 5, wherein the biomarker outcomes are regulated to lower, maintain, or raise biomarker measurements.

7. A method for biomarker-based personalized food item design, comprising the steps of:
    storing a recipe database on a non-volatile data storage device of a computing device comprising a memory, a processor, and the non-volatile storage device, the recipe database comprising a plurality of recipes, each recipe comprising a food type, a list of required ingredients and for each ingredient nutritional information;
    storing a restaurant database on the non-volatile data storage device, the restaurant database comprising a plurality of restaurant locations, each restaurant location further comprising restaurant data comprising:
        a list of available culinary skills; and
        a list of available ingredients;

storing a user profile database on the non-volatile storage device, the user profile database comprising a plurality of user profiles, each user profile comprising user preferences;

configuring a machine learning algorithm to identify associations among the user preferences, biomarker data, and the nutritional information;

using a machine learning engine operating on the computing device to:

receive, from a measurement device, biomarker data associated with a user of the measurement device;

convert the user preferences, recipes, food items, nutritional information, restaurant information, and biomarker data into a first set of vector representations;

pass the vector representations through the machine learning algorithm to identify associations among the user preferences, biomarker data, restaurant information, and the nutritional information, the identified associations comprising a required culinary skill and a list of required ingredients;

receive, from a user mobile device, a user specified biomarker goal;

convert the user specified biomarker goal into a second set of vector representations;

pass the second set of vector representations through the machine learning algorithm to obtain a best fit between the user specified biomarker goal and the identified associations, the best fit comprising a recommended food item and a recommendation for a restaurant having the required culinary skill and the list of required ingredients to prepare the recommended food item; and send the food item recommendation and the restaurant recommendation to the user mobile device.

8. The method of claim 7, wherein the biomarker data comprises biological, physiological, and/or behavioral information.

9. The method of claim 7, wherein the measurement devices comprise sensors embedded in the user mobile device and wearable technologies.

10. The method of claim 7, wherein the user preference is based on nutritional data retrieved from a third-party resource over a network.

11. The method of claim 7, wherein the user specified biomarker goal is to regulate biomarker outcomes.

12. The method of claim 11, wherein the biomarker outcomes are regulated to lower, maintain, or raise biomarker measurements.

\* \* \* \* \*